United States Patent
Sekhar et al.

(10) Patent No.: US 12,201,408 B2
(45) Date of Patent: Jan. 21, 2025

(54) METHOD OF ESTIMATING BLOOD PRESSURE OF A SUBJECT

(71) Applicant: REDARC TECHNOLOGIES PTY LTD [AU/AU], Morphett Vale (AU)

(72) Inventors: Sitansu Sekhar, Lonsdale (AU); Angus Wallace, Clovelly Park (AU)

(73) Assignee: REDARC TECHNOLOGIES PTY LTD (AU)

( * ) Notice: Subject to any disclaimer, the term of this patent is extended or adjusted under 35 U.S.C. 154(b) by 133 days.

(21) Appl. No.: 17/927,221

(22) PCT Filed: Jun. 9, 2021

(86) PCT No.: PCT/AU2021/050581
§ 371 (c)(1),
(2) Date: Nov. 22, 2022

(87) PCT Pub. No.: WO2021/248188
PCT Pub. Date: Dec. 16, 2021

(65) Prior Publication Data
US 2023/0218179 A1 Jul. 13, 2023

(30) Foreign Application Priority Data
Jun. 9, 2020 (AU) .............................. 2020901889

(51) Int. Cl.
A61B 5/021 (2006.01)
A61B 5/00 (2006.01)
A61B 5/024 (2006.01)

(52) U.S. Cl.
CPC .......... *A61B 5/02108* (2013.01); *A61B 5/725* (2013.01); *A61B 5/726* (2013.01); *A61B 5/7267* (2013.01); *A61B 5/02433* (2013.01)

(58) Field of Classification Search
CPC . A61B 5/021; A61B 5/02108; A61B 5/02416; A61B 5/02433; A61B 5/7246;
(Continued)

(56) References Cited

U.S. PATENT DOCUMENTS

| | | | |
|---|---|---|---|
| 10,327,649 B1 | 6/2019 | Mouradian et al. | |
| 2011/0196244 A1 | 8/2011 | Ribas Ripoll et al. | |

FOREIGN PATENT DOCUMENTS

| | | |
|---|---|---|
| CN | 108720821 | 11/2018 |
| WO | WO 2021248188 | 12/2021 |

OTHER PUBLICATIONS

Ibtehaz et al., "PPG2ABP: Translating Photoplethysmogram (PPG) Signals to Arterial Blood Pressure (ABP) Waveforms using Fully Convolutional Neural Networks," CoRR, Submitted on May 2020, arXiv:2005.01669, 22 pages.
(Continued)

*Primary Examiner* — Amelie R Davis
(74) *Attorney, Agent, or Firm* — Fish & Richardson P.C.

(57) ABSTRACT

The present invention relates to a method and system for estimating blood pressure of a subject. In particular, but not exclusively, the method involves receiving a photoplethysmogram (PPG) signal from a light-based Pulse-Plethysmography sensor applied to the skin of a subject and reconstructing a pulse blood pressure waveform between systolic and diastolic blood pressure of the subject. Additionally, but not exclusively, the method involves processing the pulse blood pressure waveform and reconstructing an absolute blood pressure waveform of the subject.

20 Claims, 19 Drawing Sheets

(58) Field of Classification Search
CPC ....... A61B 5/725; A61B 5/726; A61B 5/7267; A61B 5/7278
See application file for complete search history.

(56) References Cited

OTHER PUBLICATIONS

International Search Report and Written Opinion in International Appln. No. PCT/AU02021/050581, mailed on Aug. 16, 2021, 8 pages.
Li et al., "Novel wavelet neural network algorithm for continuous and noninvasive dynamic estimation of blood pressure from photoplethysmography," Sci. China Inf. Sci., Sep. 2015, 59(4):1-10.
Liang et al., "Photoplethysmography and Deep Learning: Enhancing Hypertension Risk Stratification," Biosensors (Basel). Oct. 2018, 8(4):101, 13 pages.
Sideris et al., "Building Continuous Arterial Blood Pressure Prediction Models Using Recurrent Networks," 2016 IEEE International Conference on Smart Computing, May 2016, 5 pages.
Extended European Search Report in European Appln No. 21920994.8, dated Jun. 17, 2024, 13 pages.
Johansson, "Neural network for photoplethysmographic respiratory rate monitoring," Med. Biol. Eng. Comput., May 2003, 41(3):242-248.

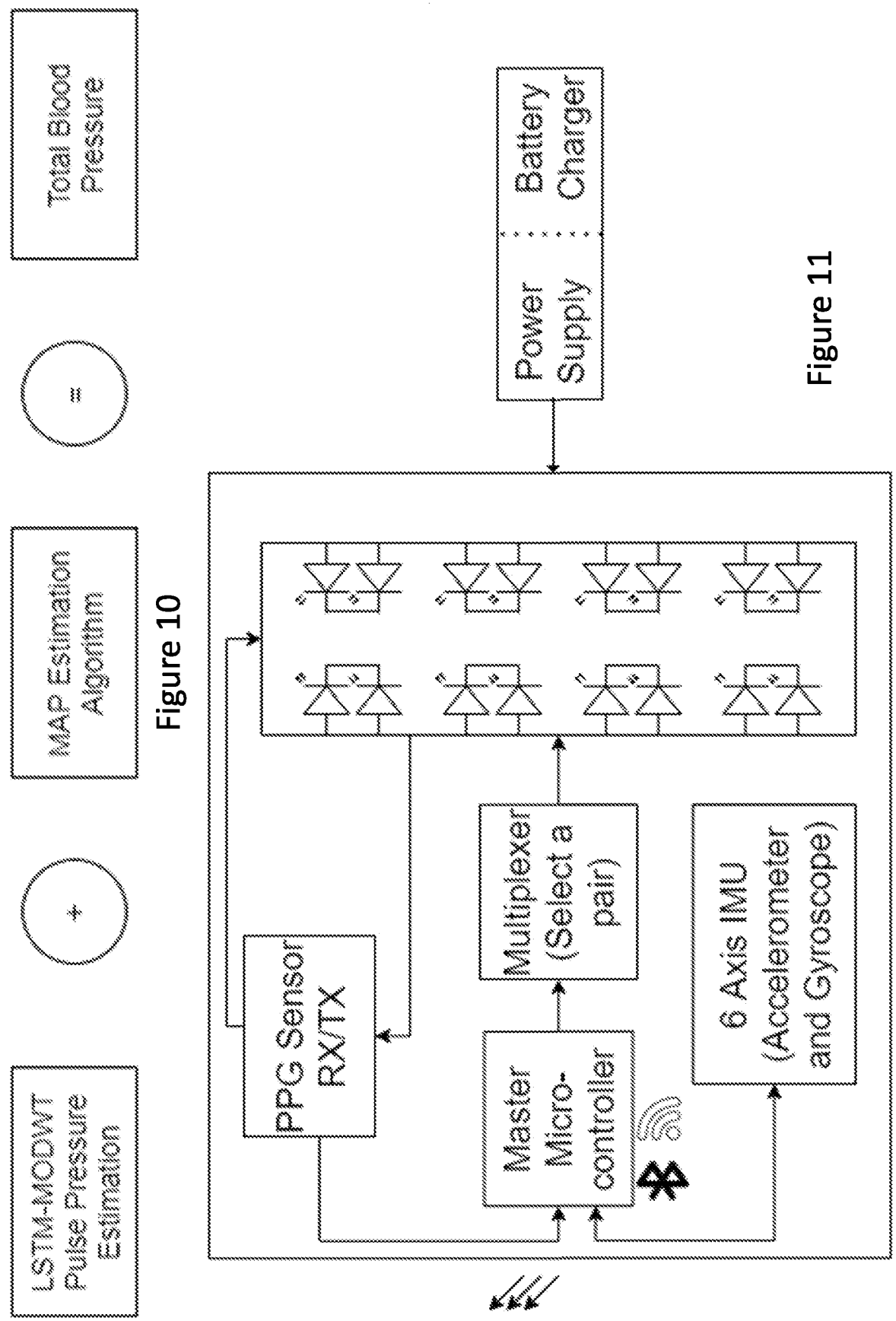

METHOD OF ESTIMATING BLOOD PRESSURE OF A SUBJECT

CROSS-REFERENCE TO RELATED APPLICATIONS

This application is a National Stage Application under 35 U.S.C. § 371 and claims the benefit of International Application No. PCT/AU2021/050581, filed Jun. 9, 2021, which claims priority to country equivalent of AU patent application No. 2020901889, filed on Jun. 9, 2020. The disclosure of each of the foregoing applications is incorporated herein by reference.

TECHNICAL FIELD

The present invention relates to a method and system for estimating blood pressure of a subject. In particular, but not exclusively, the method involves receiving a photoplethysmogram (PPG) signal from a light-based Pulse-Plethysmography sensor applied to the skin of a subject and reconstructing a pulse blood pressure waveform between systolic and diastolic blood pressure of the subject. Additionally, but not exclusively, the method involves processing the pulse blood pressure waveform and reconstructing an absolute blood pressure waveform of the subject.

BACKGROUND OF INVENTION

Blood pressure (BP) measurement in health care settings and day-to-day life helps in monitoring and diagnosing a multitude of physiological and pathological responses. Current non-invasive BP measurement systems have typically been focused on obtaining the systolic (SBP) and diastolic blood pressure (DBP) values of a subject. These systems typically use digital oscillometry techniques or various direct equation-based approaches attained from bio-signals using, for example, electrocardiogram (ECG), photoplethysmogram (PPG), pressure and sound-based sensors.

Oscillometry techniques are commonly used with pressure sensors. For example, a pump is used to inflate a rubber cuff on a subject and the results of the pressure sensor are then used to estimate the SBP and DBP levels of the subject. These techniques, however, are inaccurate and results may vary up to ±30 mmHg from the real pressure value. This inaccuracy can largely be attributed to the variance in the underlying algorithms used, which may not consider dynamic physiological changes. Further, devices employing these techniques are bulky and infeasible for portable usability. Also, 24-hour monitoring is hindered due to the discomfort of their continued use on the subject as a result of the frequent compression of the cuff required around the desired pressure measurement location.

Equation-based approaches have been under research for a significant amount of time. Non-invasive BP measurement using these approaches has typically been implemented in research studies rather than in commercial use. These approaches use various sensing systems to acquire bio-signals from a subject to develop a polynomial or logarithmic relationship with the SBP and DBP. The accuracy of these approaches, however, has typically been compromised due to the inefficiency of the equations in considering the many factors that affect blood pressure. Further, frequent calibration of devices employing these approaches is typically required to maintain an accurate measurement over time.

In particular, standard mathematical regression models typically fail to create a uniform relationship across all subjects. Also, in research, the sample size selected is typically inadequate, leading to biased models. The focus might be limited to a control group which will not generalize for an entire population including healthy subjects. Mathematical models may also focus on the present sensor estimates and do not consider the short term or the long-term physiological responses of the subjects, such as a subject suffering from an elevated pressure due to the presence of a medical professional. This may lead to false alarms or false diagnosis.

The amount of data required to create generalised mathematical models is obviously very large and it requires a very large amount of computational power compared to more specialised models. Such large databases may not be present or may be hard to access due to ethical reasons. Furthermore, a researcher is typically required to hand-select features from sensor signals based on the researcher's knowledge and findings for these models. But, these features may or may not have any correlation. Moreover, it is difficult to identify features from the sensor signals correlating to mean arterial pressure (MAP) of a subject due to, for instance, physiological differences in test subjects. Further, missing features may further lead to inaccurate estimations.

Accordingly, the current gold-standard in obtaining BP measurements is to take invasive measurements of the BP of a subject using a catheter. Invasive measurements are, however, undesirable to the subject for obvious reasons and, in some cases, may still fail to meet the required level of accuracy of within 5±8 mmHg set by Food and Drug Administration (FDA).

SUMMARY OF INVENTION

According to one aspect of the present invention, there is provided a method of estimating blood pressure of a subject, the method including: receiving a photoplethysmogram (PPG) signal from a light-based Pulse-Plethysmography sensor applied to the skin of the subject; processing the PPG signal using a Wavelet transform algorithm to derive PPG wavelet coefficients in a plurality of frequency bands; estimating blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects; and reconstructing a pulse blood pressure waveform between systolic and diastolic blood pressure of the subject from the blood pressure coefficients.

According to another aspect of the present invention, there is provided a method of monitoring blood pressure of a subject, the method including: applying a light-based Plethysmography sensor to the skin of the subject for a period of time; and estimating the blood pressure of the subject according to the above method at designated intervals over the period time.

According to another aspect of the present invention, there is provided a system for estimating blood pressure of a subject, the system including: a light-based Pulse-Plethysmography sensor configured to be applied to the skin of the subject to generate a photoplethysmogram (PPG) signal; a processor in data communication with the sensor; a memory; and software resident in the memory and accessible to the processor, the software including a series of instructions executable by the processor to configure the processor to: process the PPG signal using a Wavelet transform algorithm to derive PPG wavelet coefficients in a plurality of frequency bands; estimate blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects; reconstruct a pulse blood pressure waveform between systolic and diastolic blood pressure of the subject from the blood pressure coefficients; and output the pulse blood pressure waveform to a display.

The method uses a machine learning algorithm to estimate blood pressure coefficients by processing derived PPG wavelet coefficients. Existing machine learning techniques, such as standard regression models, support vector machines, classification and regression trees (CART) and neural networks, could be used to predict systolic and diastolic blood pressures from a PPG signal. Doing so, however, would require an impractical and uncountable number of features for input to the machine learning algorithms to achieve a high level of accuracy in predicting the SBP and DBP. The justification for the use of these features may thus become random or heuristic. Further practical implementation of searching such features becomes computationally intensive and exhaustive too—missing features which may result in the incorrect estimation of the pressure values.

The power of machine learning can be used in extracting and comprehending features automatically rather than manual extraction with human interference. From a physiological perspective, this is essential due to the quasi-static nature of the human body. Preferably, the method uses a semi-supervised approach in blood pressure estimation, enabling an accurate estimation focusing the machine learning algorithm on aspects where human intelligence may overlook. The method is incorporated into a non-invasive, non-pressurised system for estimating BP of a subject. This non-invasive, non-pressurised system enables portable and continuous monitoring of the subject without hindering daily activity of the subject. Further, such a system can replace the above described invasive systems in circumstances where, for example, monitoring of BP might be essential but not critical in certain areas of hospitals.

In an embodiment, the light-based Pulse-Plethysmography sensor includes a light source having an emission wavelength and a photodiode having a detection wavelength, wherein the emission wavelength and the detection wavelength are around an isosbestic wavelength where oxygenated and deoxygenated blood absorbs same amount of light. For example, the light source is an Infrared (IR) light source. The reconstruction of the pulse blood pressure waveform is thus able to be achieved non-invasively. While this embodiment implements an isosbestic sensor, it will be appreciated by those persons skilled in the art that the method and system could be configured to use a sensor incorporating wavelengths anywhere from the visible spectrum to the infra-red spectrum. The isosbestic sensor at the infra-red wavelength is preferable as it compensates for the equal absorption by oxygenated and de-oxygenated blood and is less susceptible to motion artefacts. An estimation of BP using the isosbestic sensor may therefore be more confident about the underlying physiological changes being homeostatic rather than interference from external motion.

In an embodiment, the light-based Pulse-Plethysmography sensor includes two or more pairs of the light source and the photodiode, and the method further includes determining a signal to noise ratio (SNR) of the PPG signal from each of the pairs of the light source and the photodiode, and selecting one of the pairs of the light source and the photodiode for providing the PPG signal with the best SNR.

In an embodiment, the method further includes receiving an inertial measurement signal from an inertial measurement unit (IMU) adjacent the light-based Pulse-Plethysmography sensor, and compensating for motion artefacts when determining the SNR of the PPG signal from each of the pairs of the light source and the photodiode includes using the inertial measurement signal.

In an embodiment, the method further includes processing selected ones of the PPG wavelet coefficients using the machine learning algorithm based on an energy level present at each of the frequency bands exceeding a threshold level. The method may further include providing the selected ones of the PPG wavelet coefficients in a 2-Dimensional matrix of features to the machine learning algorithm. Further, each column of the 2-Dimensional matrix is autoregressive incorporating near past and near future samples of the selected ones of the PPG wavelet coefficients. Alternatively, the method may provide the PPG wavelet coefficients as a 1-Dimensional vector incorporating the reconstructed wavelet of specific decomposed wavelet level of blood pressure. Further, multiple 1-Dimensional vectors of reconstructed wavelets of all desired levels of blood pressure in 0.5-8 Hz bandwidth may be provided.

In an embodiment, the machine learning algorithm is a Recurrent Neural Network (RNN) algorithm, such as a Long short-term memory (LSTM) model. Preferably, the method further includes processing the PPG wavelet coefficients using multiple LSTM models.

That is, embodiments of the invention provide for the estimation and reconstruction of a pulse blood pressure waveform to be achieved algorithmically using a Wavelet signal processing technique along with a memory-based machine learning algorithm of Long Short-Term Memory (LSTM). One benefit of using LSTM networks relates to the ability to account for dynamically changes in the body of the subject by considering short and long past states of the body under homeostasis. The abovementioned existing machine learning techniques or direct equation-based approaches mostly depend on present values from the sensors and fail to incorporate dynamic changes. Further, the use of the Wavelet transform algorithm involves obtaining components of the PPG signal at different frequency bandwidths to develop a more time-frequency based continuous model.

Further, embodiment of the invention using LSTM along with the Wavelet transform algorithm enable a time-frequency based analysis of the PPG signal. The Wavelets algorithm decomposes the PPG signal into different frequency bands. The PPG wavelets coefficients in each of the frequency bands are organised into 2-Dimensional matrix representation which is a feature to the neural network model. LSTM neural network models are developed to establish a correlation between the PPG wavelet coefficients in specific frequency bands with that of Invasive Arterial Blood Pressure (ABP) wavelet coefficients. These correlations are used in time series reconstruction of ABP wavelet coefficients. In the embodiment, the method further includes reconstructing output of the multiple LSTM models to form the pulse blood pressure waveform using an inverse Wavelet transform algorithm.

In an embodiment, the Wavelet transform algorithm is a Maximally Overlapped Discrete Wavelet Transform (MODWT) algorithm, and the method further includes reconstructing the pulse blood pressure waveform using an inverse MODWT algorithm. That is, embodiments of the method provides for the calculation of a pulse pressure, AP, following sequential method steps involving signal processing techniques with MODWT and memory-based recurrent neural network (RNN) estimation.

In an embodiment, the method further includes preprocessing the PPG wavelet coefficients before processing using the machine learning algorithm by low-pass filtering the PPG wavelet coefficients with a cut-off frequency for the frequency bands. For example, the cut-off frequency is 10 Hz.

In an embodiment, the method further includes: processing the pulse blood pressure waveform using a further Wavelet transform algorithm to derive pulse blood pressure wavelet coefficients in a plurality of frequency bands; extracting features from the pulse blood pressure wavelet coefficients in the plurality of frequency bands; estimating mean arterial blood pressure (MAP), systolic blood pressure (SBP) or diastolic blood pressure (DBP) coefficients by processing the features using a further machine learning algorithm that has been trained on the training data; and reconstructing the MAP, SBP and or DBP waveforms from the MAP, SBP and or DBP coefficients, respectively.

Preferably, the method further includes combining the pulse blood pressure waveform and one or more of the MAP, SBP or DBP waveforms to reconstruct an absolute blood pressure waveform of the subject.

In an embodiment, the further machine learning algorithm is a Convolutional Long short-term memory (ConvLSTM) network and the features are a 2-Dimensional feature matrix including temporal and spatial features of the pulse blood pressure wavelet coefficients.

In an embodiment, the method further includes estimating intermediate MAP, SBP or DBP coefficients using the ConvLSTM network.

In an embodiment, the method further includes: selecting features of the PPG signal and the pulse blood pressure waveform; and estimating further intermediate MAP, SBP or DBP coefficients by processing the features of the PPG signal and the pulse blood pressure waveform using deep neural networks, respectively, that have been trained on the training data.

In this embodiment, the method further includes: concatenating the intermediate and further intermediate MAP, SBP or DBP to form a concatenated output vector; and passing the output vector through multiple layers of hidden neurons in an output network to generate the estimated MAP, SBP or DBP coefficients.

In an embodiment of the system, the processor is further configured to: process the pulse blood pressure waveform using a further Wavelet transform algorithm to derive pulse blood pressure wavelet coefficients in a plurality of frequency bands; extract features from the pulse blood pressure wavelet coefficients in the plurality of frequency bands; estimate mean arterial blood pressure (MAP), systolic blood pressure (SBP) or diastolic blood pressure (DBP) coefficients by processing the features using a further machine learning algorithm that has been trained on the training data; and reconstruct the MAP, SBP and or DBP waveforms from the MAP, SBP and or DBP coefficients, respectively. Preferably, the processor is further configured to: combine the pulse blood pressure waveform and one or more of the MAP, SBP or DBP waveforms to reconstruct an absolute blood pressure waveform of the subject; and output the absolute blood pressure waveform to the display.

BRIEF DESCRIPTION OF DRAWINGS

Embodiments of the present invention will now be described with reference to the accompanying drawings, wherein:

FIG. 10 is a block diagram showing a method of estimating blood pressure of a subject in accordance with an embodiment of the present invention;

FIG. 11 is a block diagram showing hardware for estimating blood pressure of a subject in accordance with an embodiment of the present invention;

DETAILED DESCRIPTION

Figures 1, 2:
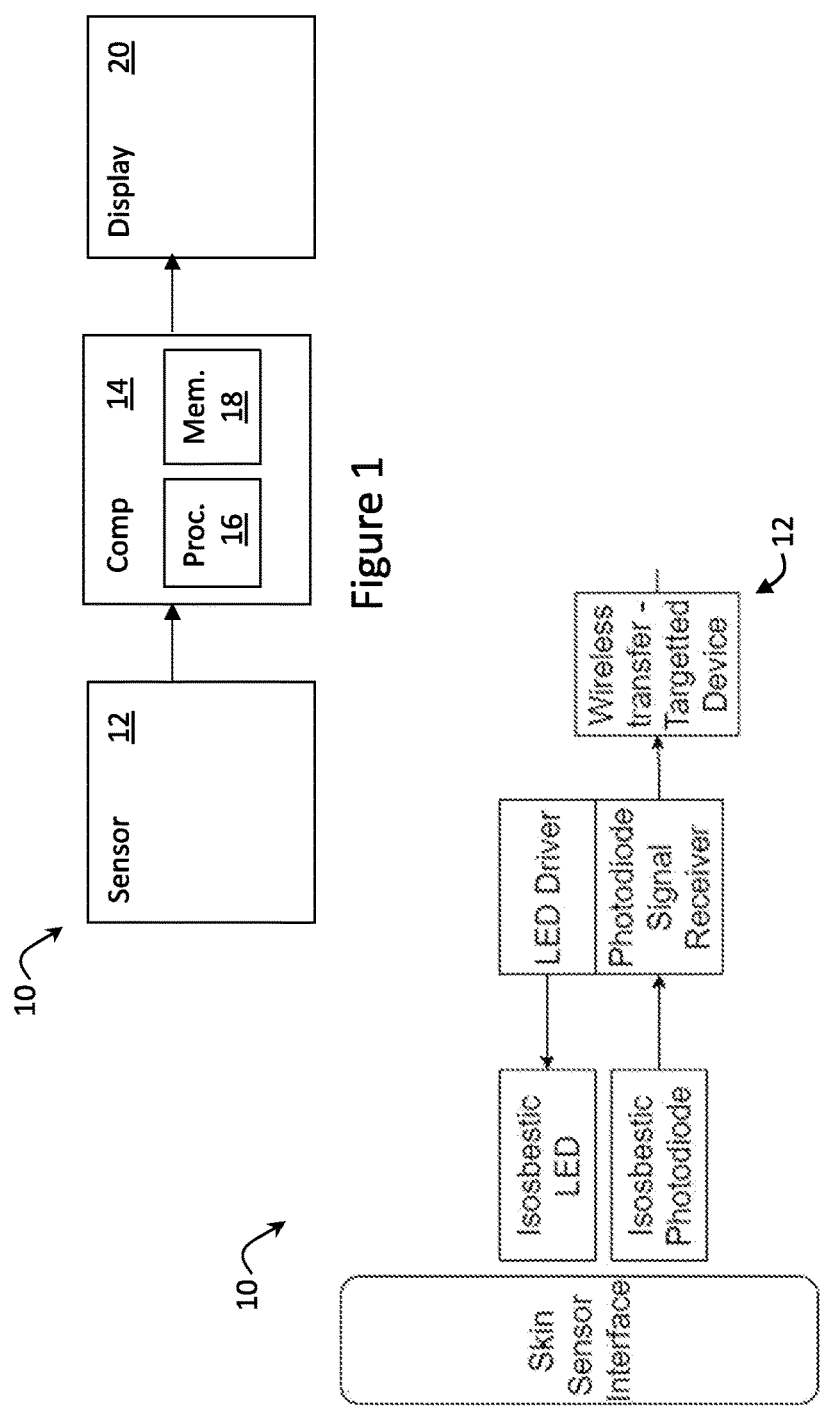
FIG. 1 is a block diagram showing a system for estimating blood pressure of a subject in accordance with an embodiment of the present invention.
FIG. 2 is a flow chart showing a system for estimating blood pressure of a subject in operation in accordance with an embodiment of the present invention.

FIG. 1 shows an embodiment of a system 10 for estimating blood pressure of a subject non-invasively. The system 10 includes a light-based Pulse-Plethysmography sensor 12 that is configured to be applied to the skin of a subject to generate a photoplethysmogram (PPG) signal. The sensor 12 is applied to the skin by being attached, using a suitable attachment means, to a desired location on the body, such as a finger or wrist, of the subject. The sensor 12 includes a light source and a photodiode to detect light reflected from the subject. For example, the sensor 12 includes an Infrared (IR) LED light source with an emission wavelength driven by an LED driver around an isosbestic wavelength where oxygenated and deoxygenated blood absorbs the same amount of light. The photodiode also has a detection wavelength around the isosbestic wavelength.

The system 10 further includes a computer 14 in data communication with the sensor 12. The data connection may be wired or wireless. For example, the PPG signal is received via Bluetooth or WIFI. The computer 14 includes a processor 16 in data communication with a memory 18. The memory 18 includes software that includes a series of instructions executable by the processor 16 to configure the processor 16 to perform a number of steps when the system 10 is in the implementation phase.

The processor 16 processes the PPG signal received wirelessly from the sensor 12 using a Wavelet transform algorithm, such as a Maximally Overlapped Discrete Wavelet Transform (MODWT) algorithm, to derive PPG wavelet coefficients in a plurality of frequency bands. As mentioned, the PPG signal is acquired from the body of the subject at the range of the isosbestic wavelength. It is then pre-processed, re-sampled and decomposed with the MODWT algorithm which is discussed below in more detail.

The processor 16 then estimates blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects. The training of the machine learning algorithm was conducted prior to the implementation phase and, in one embodiment, is a neural network algorithm which gives a time-frequency estimation of blood pressure coefficients at multiple frequency bandwidths.

The processor 16 then reconstructs a pulse blood pressure waveform between systolic and diastolic blood pressure of the subject from the blood pressure coefficients using an inverse Wavelet transform algorithm, such as an inverse MODWT algorithm. Finally, the processor 16 outputs the pulse blood pressure waveform to a display 20. The display of the pulse blood pressure waveform on the display 20 enables the blood pressure of the subject to be monitored by, for example, care professionals when the sensor 12 is applied to the skin of the subject for a period of time.

FIG. 2 shows another embodiment of the system 10 in operation in the implementation phase. In this embodiment, the sensor 12 is shown to include a number of components that are used to generate the PPG signal and transmit it to the computer 14. That is, the senor 12 includes a skin sensor interface for attaching the sensor 12 to the desired location on the body. The sensor 12 includes an isosbestic LED, driven by an LED driver, and an isosbestic photodiode with a photodiode signal receiver which receives the PPG signal sampled at a specific sampling frequency Fs. The PPG signal is then transmitted using a wireless transmitter of the sensor 12 to the computer 14 to undertake the abovementioned processing including machine learning processing and reconstruction.

The computer 14 firstly undertakes pre-processing of the received PPG signal, which involves low pass filtering with a cut-off frequency at 20 Hz. In this frequency range, the expectation of higher physiological response is present. Higher frequency components in the signal are due to the presence of external interference. A check may be further conducted if the signal is valid or not through a motion removal artefact algorithm. The result of the pre-processing step is a normalised PPG signal between 0-1.

The computer 14 then carries out a Maximally Overlapped Discrete Wavelet Transform (MODWT) algorithm on the normalised PPG signal. This generates different levels of coefficients at different frequency bands. n specific frequency bandwidths are selected which have maximum information about the physiological changes. The output vector from each frequency bandwidth is structured into a 2-Dimensional matrix. This matrix is designed to be autoregressive with an expectation of the current value of prediction to be depended on f past samples and f−1 future samples, giving it a non-causal representation.

The restructured 2-D matrix at each frequency bandwidth is presented to a trained machine learning algorithm. In the embodiment, the machine learning algorithm includes multiple Long short-term memory (LSTM) models. n LSTM models generate n vectors of wavelet coefficients representing an estimation of blood pressure wavelet coefficients. These coefficients are then passed through an Inverse Maximally Overlap Discrete Wavelet Transform (IMODWT) algorithm to generate a reconstructed differential (pulse) pressure waveform, ΔP.

Training Phase

Figure 3:
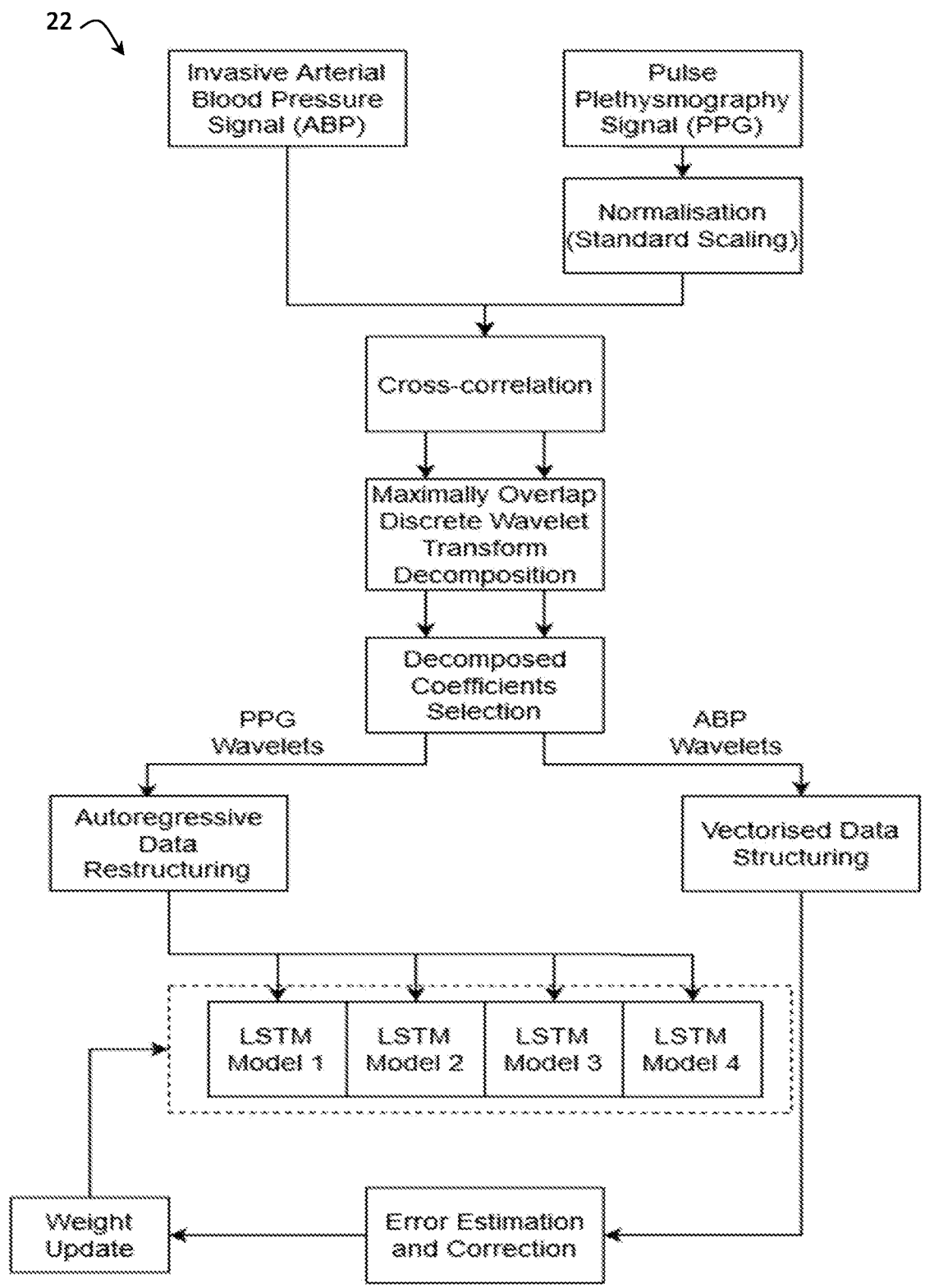
FIG. 3 is a flow chart showing a method of training a machine learning algorithm in accordance with an embodiment of the present invention.

An embodiment of the training phase of the machine learning algorithm of the system 10 is shown in the flow chart 22 of FIG. 3. As mentioned, the training data for the machine learning algorithm includes PPG wavelet coefficients derived from PPGs from test subjects correlated with Invasive Arterial Blood Pressure (ABP) wavelet coefficients derived from simultaneously obtained ABP measurements. More specifically, the ABP measurements and PPG signals recorded from several test subjects simultaneously were obtained through an ethics approval process from the MIMIC-II database for the system 10. The de-identified waveforms from the test subjects were pre-processed and filtered. The initial sampling of the signals was conducted at 500 Hz. It was determined that such high sampling is not required as the desired interest of frequency bands were below 20 Hz. A resampling at 125 Hz was thus done for the signals. It was determined that the choice of the sampling frequency at 125 Hz here is heuristic, and a lower sampling frequency can be chosen. Two signals were structured, starting from the same timestamp.

The PPG signals were normalised as the recording from different patients were undertaken using different devices having different voltage output. Cross-Correlation between the two signals was undertaken. The cross-correlation ensured to estimate the phase lag between the two signals.

$$r(t) = ABP(t) \otimes PPG(t) = \int_{-\infty}^{\infty} ABP(\tau)PPG(\tau + t)d\tau \quad (1)$$

The cross-correlation estimate r(t) in equation (1) is used for the calculation of the maximum lag, $$\varepsilon = t[r(t)|_{max(r(t))}] \quad (2)$$

This phase lag, & is generated because of the different locations of the recording undertaken for the pressure and the PPG in the patients. The PPG signal is shifted forward (or backward) based on the lag. This was essential as the lag is a variable depending on the distance between the placement of the two sensors on the patient. Since this is an unknown variable, it creates uncertainty in the estimates in blood pressure in model training.

MODWT Transform

Maximally overlap discrete wavelet transform (MODWT) is used for the decomposition of the signal. Compared to the standard wavelet transform (DWT), MODWT undertakes a multi-resolution analysis of the signal. The size of the coefficients for all levels are defined for all sample sizes. No decimation occurs for subsequent frequency bands coefficients, unlike standard DWT.

The retainment of the same number of coefficients enables in developing an input-output time-series relationship in different frequency bandwidths. Whereas, DWT coefficients do not provide any time-series correlation due to their time-varying property.

In MODWT, the signal is passed through a set of high pass and low pass quadrature mirror filters. There have been several different types of quadrature mirror filters proposed in theory such as Daubechies, Symlets, Coiflets, Mexican Hat etc. The choice of the filter is based on the correlation between the shape of the signal with that of the filter response. The current shape of the PPG and ABP signal had a maximum correlation with the Daubechies filter with 4 vanishing moments ('db4'). The flexibility of the design allows in choosing any filter and training the neural networks based on that filter. In the current embodiment, a choice of db4 has been preferred.

The coefficients of the 'db4' or any chosen filter have high pass coefficients denoted by $h_l$ and low pass coefficients denoted by $g_l$. The signal is iteratively passed through the set of these filters for n times, where $n \in \{1,2 \ldots \}$. The total number of times, n, is depended on the length of the signal in consideration. The present embodiment considers a signal length of L sampled at $F_s$ for both PPG and ABP signals. The number of decomposition level, n in present case comes out to be:

$$n = [\log_2 L] \quad (3)$$

The iterative decomposition of ABP and PPG using the circular filter operation gives detailed high-pass components represented in equations (4) and (5).

$$\psi(PPG)_{n,t} = \sum_{l=0}^{L-1} \tilde{h}_{nl} \times PPG_{t-l} \times \mod(L) \quad (4)$$

$$\psi(ABP)_{n,t} = \sum_{l=0}^{L-1} \tilde{h}_{nl} \times ABP_{t-l} \times \mod(L) \quad (5)$$

Here, n is decomposition level, with $n \in 1,2 \ldots, \log_2 L$
L being the signal length
$h_{nl}$ being the coefficient of high pass filter periodised to signal length L.

Similarly, the iterative approach yields the approximation components represented in equation (6) and (7)

$$\phi(PPG)_{n,t} = \sum_{l=0}^{L-1} \tilde{g}_{nl} \times PPG_{t-l} \times \mod(L) \quad (6)$$

$$\phi(ABP)_{n,t} = \sum_{l=0}^{L-1} \tilde{g}_{nl} \times ABP_{t-l} \times \mod(L) \quad (7)$$

$g_{jl}$ being the coefficient of the low pass filter periodised to signal length L.

The relationship of the coefficients $h_{nl}$ and $g_{nl}$ with that of the selected filter which in this innovation was chosen to be 'db4' at every iteration is modified through the scaling given by:

$$\tilde{g}_{nl} = \frac{g_l}{\sqrt{2^n}} \quad (8)$$

$$\tilde{h}_{nl} = \frac{h_l}{\sqrt{2^n}}$$

The iterative decomposition provides vectors of $\psi(ABP)_{n,t}$ and $\psi(PPG)_{n,t}$ which are significant for innovation. The low pass components of the MODWT decomposition, i.e. $\psi(PPG)_{n,t}$ and $\psi(ABP)_{n,t}$ are ignored at each level are ignored. But in the nth decomposition level of PPG and ABP, $\psi(PPG)_{n=n,t}$ and $\psi(ABP)_{n=n,t}$ is obtained, which is set to 0. This involves the low pass component containing the mean of the signal. While PPG is demeaned resulting in 0 energy at DC level, the ABP signal has a non-zero mean containing the Mean Arterial Pressure whose estimation is described below.

The filter responses are determined for a signal length L chosen to be 250. The responses demonstrate the changing bandpass filtering cut-off frequency with every subsequent MODWT iteration with filter 1 having the highest cut-off frequency at $f_c = f_s/2^2$, filter 2 at $f_s/2^3$ and so on. The final iteration which is at $n = \log_2 250 \approx 7$ yields a final low pass component which is ignored.

The circular filter operation in equations (4) and (5) generates a convolution between the periodised high pass filter coefficients at each level with that of the signal giving a one-dimensional vector of decomposed signal MODWT coefficients. The periodisation converts the filter coefficient at level n to a L x L square matrix giving the form of the matrix, where X represents either the PPG or ABP.

For n levels of decomposition, a 2-dimensional matrix for ABP and PPG are formed containing the high-frequency components, $$\psi(X) = \begin{bmatrix} \psi_1(X[t]) \\ \psi_2(X[t]) \\ \vdots \\ \psi_n(X[t]) \end{bmatrix} \quad (9)$$

Data Structuring

The structuring of the data involved first the selection of the decomposed coefficients is shown in FIG. 2. The selection of the coefficients was based on the energy level present at each level. The idea is to incorporate those wavelet coefficients bands for PPG and ABP, which adds to the significant amount of energy. Since the estimation requirement is that of ABP, the energy of the decomposed detailed coefficients for ABP were analysed. Through the data analysis, it was obtained to be in a signal length of L, the maximum density of energy is concentrated in j number of bands, where j ⊂ n. Only those wavelet bands are selected where the concentration of the energy adds up to 95% or more.

Figure 4:
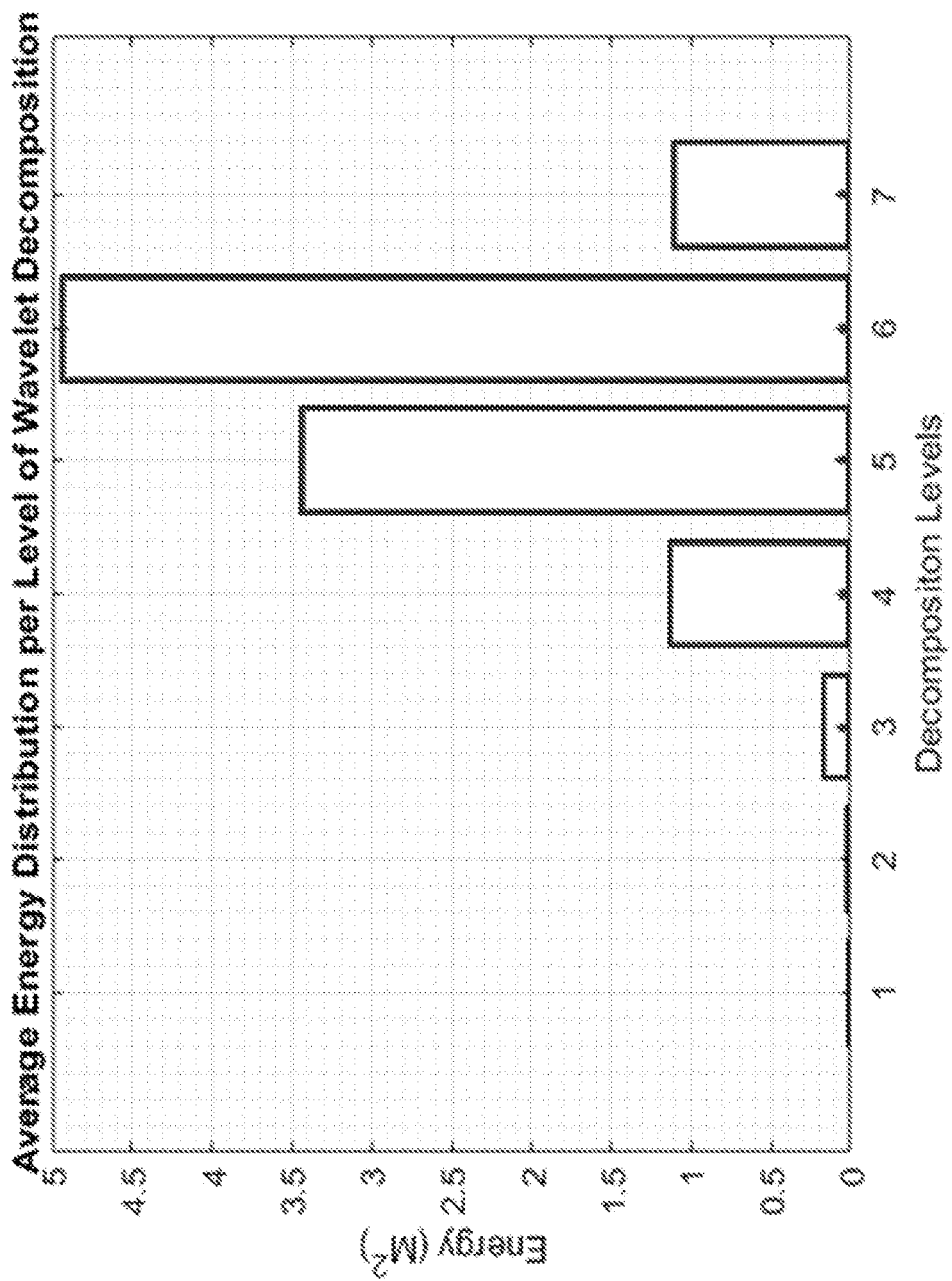
FIG. 4 is a graph showing an energy distribution of MODWT coefficients for ABP.

In a wavelet decomposition of the signal length of L=250 and n=7, the values of j are obtained to be in levels 4-7. The bar graph in FIG. 4 is evident of the levels 4-7 being the coefficients containing the highest concentration of energy. Wavelets in these levels were significant while other remaining levels were zeroed, resulting in:

$$\psi(X) = \begin{bmatrix} 0 \\ 0 \\ 0 \\ \psi_4(X[t]) \\ \psi_5(X[t]) \\ \psi_6(X[t]) \\ \psi_7(X[t]) \end{bmatrix} \quad (10)$$

Each resulting decomposed wavelet detailed coefficients of PPG, $\psi_j(PPG[t])$ is organised into an autoregressive 2-D matrix representation, $\psi_j(PPG[t])$. The dimension of the 2D matrix is f×L. Here, f∈$Z^+$, is used as a set of features for the neural networks to consider to estimate the present ABP $\psi_n[t=t_{present}]$ based on some of the past and future samples. The generalised representation of the 2D matrix representation for a level n gives:

$$\Psi_j(PPG[t]) = \begin{bmatrix} \psi_j\left(PPG\left[t-\frac{f}{2}\right]\right) & \psi_j\left(PPG\left[t-\frac{f}{2}+1\right]\right) & \cdots & \psi_j\left(PPG\left[t+L-\frac{f}{2}+1\right]\right) & \psi_j\left(PPG\left[t+L-\frac{f}{2}\right]\right) \\ \psi_j\left(PPG\left[t-\frac{f}{2}+1\right]\right) & \psi_j\left(PPG\left[t-\frac{f}{2}+2\right]\right) & \cdots & \psi_j\left(PPG\left[t+L-\frac{f}{2}\right]\right) & \psi_j\left(PPG\left[t+L-\frac{f}{2}+1\right]\right) \\ \vdots & \vdots & \ddots & \vdots & \vdots \\ \psi_j(PPG[t]) & \psi_j(PPG[t+1]) & \cdots & \psi_j(PPG[t+L-1]) & \psi_j(PPG[t+L]) \\ \vdots & \vdots & \ddots & \vdots & \vdots \\ \psi_j\left(PPG\left[t+\frac{f}{2}-2\right]\right) & \psi_j\left(PPG\left[t+\frac{f}{2}-1\right]\right) & \cdots & \psi_j\left(PPG\left[t+L+\frac{f}{2}-3\right]\right) & \psi_j\left(PPG\left[t+L+\frac{f}{2}-2\right]\right) \\ \psi_j\left(PPG\left[t+\frac{f}{2}-1\right]\right) & \psi_j\left(PPG\left[t+\frac{f}{2}\right]\right) & \cdots & \psi_j\left(PPG\left[t+L+\frac{f}{2}-2\right]\right) & \psi_j\left(PPG\left[t+L+\frac{f}{2}-1\right]\right) \end{bmatrix} \quad (11)$$

From each signal of length L, wavelet decomposed to levels n and considering the highest energy concentration of the wavelet coefficients only in levels j, gave length of j equivalent number of 2-D matrices.

The output ABP for each significant level, j was arranged in vectorized form giving, $$\psi_j(ABP[t])=[\psi_j(ABP[t]),\psi_j(ABP[t+1]), \ldots ,\psi_j(ABP[t+L])] \quad (12)$$

LSTM Neural Network

Long short-term memory (LSTM) is a variant of neural networks. They have internal gates. These gates ensure the information it is obtaining from the previous values are selectively read, selectively forgotten and selectively written. This selective process makes the LSTM efficient in remembering only crucial information from the past rather than everything.

The structure of a neuron of an LSTM consist of forgetting, read, write and state gates. These gates have associated parameters-weights and biases, which are learnt through the process of feedforward and back-propagation. The size of the weights and biases are depended on the designer of the neural networks and the purpose for which it is designed. In the present innovation, the single LSTM neuron has been assumed to have a units. These units are the matrix sizes of the parameters inside which have to be learnt in the training process. There are 12 essential parameters associated with the 4 essential gates required to be learnt. These include the recurrent weights given by $W_x$, kernel input weights are given by $U_x$ and biases $b_x$.

$$\text{Parameters} = \begin{pmatrix} W_i, U_i, b_i \\ W_f, U_f, b_f \\ W, U, b \\ W_o, U_o, b_o \end{pmatrix} \quad (13)$$

Figure 5:
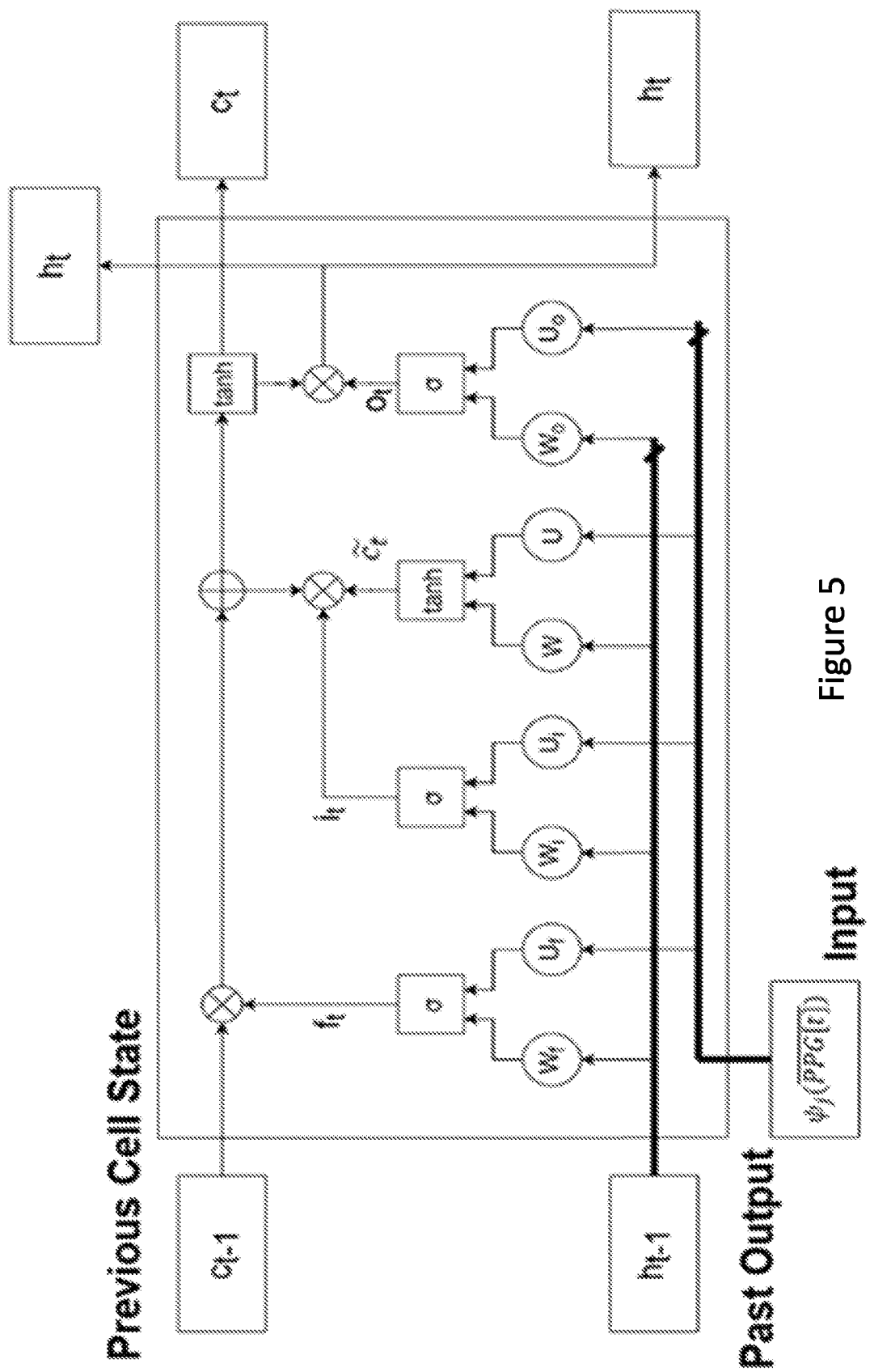
FIG. 5 is an example of a Long short-term memory (LSTM) neuron structure.

The neuron structure of an LSTM is shown in FIG. 5. The neuron receives information from the previous time-step in the form of the estimated output $h_{t-1}$ and the cell state $C_{t-1}$. The Previous Cell State contains the information of factors such as what has been remembered, read and written in the previous state. It may also include what has been forgotten in the previous state. The Past Output $h_{t-1}$ is the output from the previous time-step. In its simplistic form, it is the predicted output of the wavelet coefficient of $\psi_j(ABP[t-1])$.

The input to a single neuron as shown in FIG. 5 is the column vector at time t of 2D matrix $\psi_j(PPG[t])$ of level j. The column vector contains-past samples and $$\frac{f}{2}-1$$

future samples from present time state t. The vector input along with gates estimate the output ht.

Internally the first gate is the forget gate. The information it is acquiring from the previous state is modified to incorporate the information from the past and forget unwanted or less involved information. The output range of $f_t$ is between 0 and 1.

The next gate is the input which decides what information from the present input $\psi_j(PPG[t])$ must be read. This selective reading is acquired through the process of learning to enable it to have selective feature selection extraction.

The third cell stage is the temporary cell state, ct. The temporary cell state is used for the modification of the previous cell state, incorporating the information from the present input as well.

Finally, the output, $o_t$ ensures selective writing in predicting the present output.

The present cell state, $C_t$ and present cell output $h_t$ is given by:

$$C_t = f_t \times C_{t-1} + i_t \times C_t$$

$$h_t = o_t \times \tanh C_t \quad (14)$$

A recursive dependency is observed from (14), with the output depending on the different gates, which in turn depends on the previous states.

Neural Network Structure and ABP Coefficients Estimation

Figure 6:
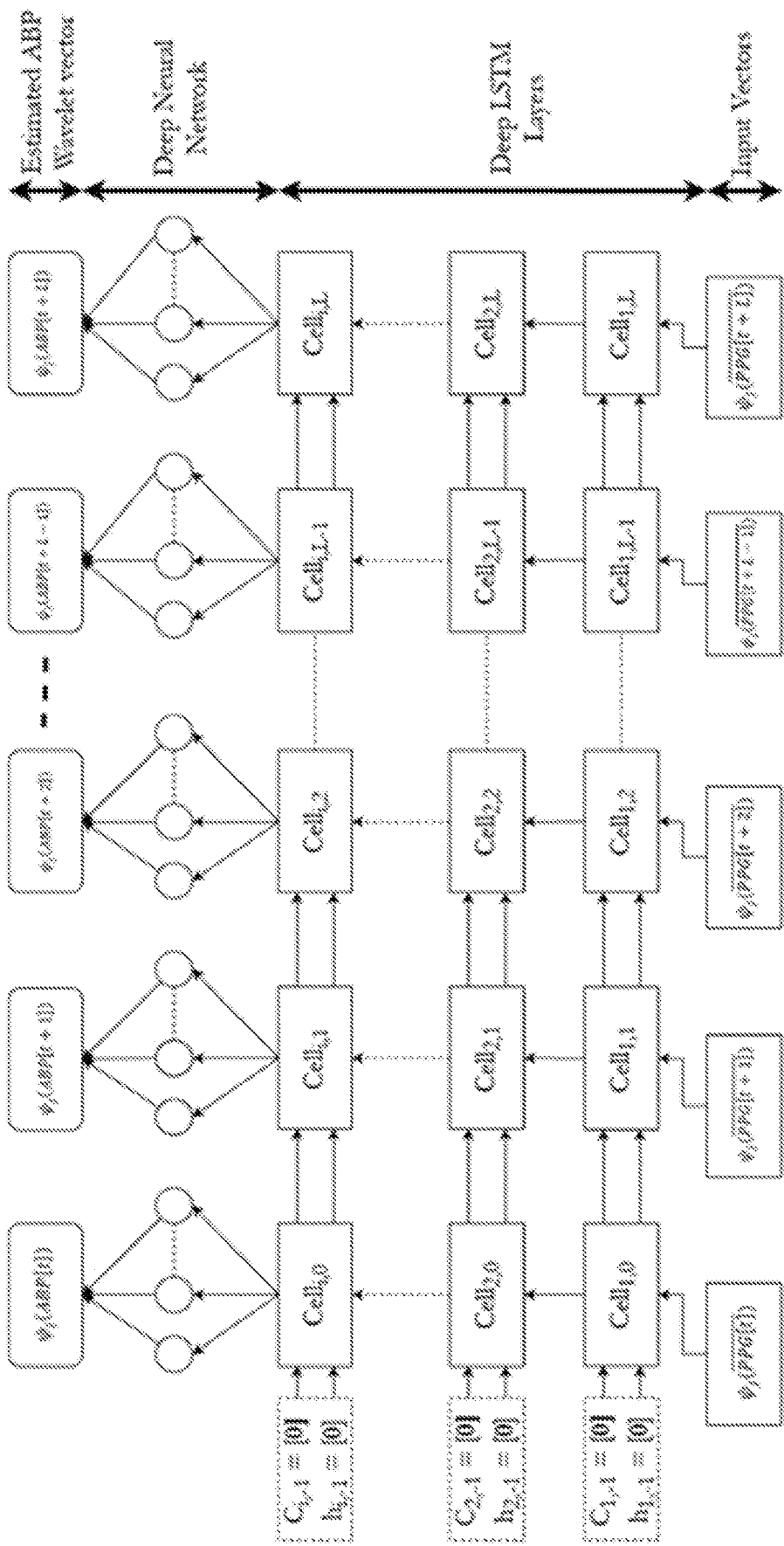
FIG. 6 is an example of a Deep LSTM neural network.

The overall design of the expected neural network is shown in FIG. 6. This is a representation of the deep LSTM which is used for the estimation of a single wavelet coefficient at level j from the structured matrix of PPG wavelet at that level. A multi-layer LSTM is preferred to estimate the non-linear patterns in the dynamic nature of the body.

Each layer of the LSTM neural network follows L number of cells based on the signal length L. This spans over a depth of i consisting of different structural layers. The flexibility of the design allows changing the value of i based on the accuracy of the system. But larger values of i would require higher computation power and may cause overfitting leading to inaccuracy in the actual result. Current innovation involves the use of i to be 3 layers.

In the current innovation, at each layer, the number of units present inside each neuron is varied which changes the number of Parameters to be learnt to develop a complex time-based correlation. Further, the initialisation of the LSTM states $C_t$ and $h_t$ initially at every cell level was set to empty matrix 0.

The final deep LSTM layers are followed by a single deep layer of artificial neural network. This is used to combine the estimates of the output matrices $h_t$ in the LSTM layer i and provide a single wavelet pressure estimate $\psi_j(ABP[t])$. The subsequent ABP wavelet estimates are a complex combination of the past estimates in every layer giving a final output of a vector consisting of $\psi_j(ABP[t])$.

In the training phase, a standard back-propagation technique is used in learning the Parameters. This is done through the feedback of the output error generated at every epoch on the training data (obtained from the MIMIC-II database) with the ground truth pressure wavelets and propagating the error backwards. This backpropagation of the error results in the update of the weights, as shown in FIG. 3. Furthermore, based on the number of desired levels under consideration possessing a significant amount of energy, that many numbers of LSTM neural networks were trained, which in this case is the number of levels, j. In a preferred implementation, the number of structures trained was 4 with a signal length of L=250.

Once the weights of all the layers are learnt, the implementation phase involves structuring and presenting the inputs to the network, which accumulates and multiplies the values to obtain the final estimated output vector.

Reconstruction of Pulse Pressure Waveform

The reconstruction of the pulse pressure waveform follows the output vectors generated by the length of j number of LSTM for each level. The output vector contains $$\psi(ABP[t]) = \begin{bmatrix} \psi_{j(1)}(\overline{ABP[t]}) \\ \psi_{j(2)}(\overline{ABP[t]}) \\ \vdots \\ \psi_{j(len(j))}(\overline{ABP[t]}) \end{bmatrix} \quad (15)$$

Knowing the fact that the reconstruction is depended on the levels which have been considered in the LSTM models were significant, and the levels which were not included in the LSTM estimation especially the coefficients lying in higher frequency bandwidth were zeroed, forming a 2D vector of size $(\log_2 L) \times L$, $$\psi(ABP[t]) = \begin{bmatrix} 0 \\ 0 \\ 0 \\ \psi_{j_1}(X[t]) \\ \psi_{j_2}(X[t]) \\ \psi_{j_3}(X[t]) \\ \psi_{j_4}(X[t]) \end{bmatrix} \quad (16)$$

The reconstruction filter involves the use of complementary filters of the analysis decomposition filter. In the current innovation, using Daubechies filter, 'db4' and applicable to any other wavelet filters in the family of wavelets, the relationship between the h which is the decomposition filter with that of $hr_l$.

The inverse MODWT reconstruction is obtained by:

$$X(t) = \sum_{j=1}^{n} \sum_{l=0}^{L-1} \widetilde{hr}_{j,l} \psi_j(X[t]) + \sum_{l=0}^{L-1} \widetilde{gr}_{j,l} \phi_{j=j_0}(X[t]) \quad (17)$$

In equation (17), the latter part involving the low pass component with $\phi_j$ is insignificant in the present embodiment as the DC components have not been involved in the reconstruction using LSTM. Hence equation (17) reduces to:

$$X(t) = \sum_{j=1}^{n} \sum_{l=0}^{L-1} \widetilde{hr}_{j,l} \psi_j(X[t]) \quad (18)$$

$$X(t) = \sum_{l=0}^{L-1} \widetilde{hr}_{j_1,l} \psi_{j_1}(X[t]) + $$

$$\sum_{l=0}^{L-1} \widetilde{hr}_{j_2,l} \psi_{j_2}(X[t]) + \sum_{l=0}^{L-1} \widetilde{hr}_{j_3,l} \psi_{j_3}(X[t]) + \sum_{l=0}^{L-1} \widetilde{hr}_{j_4,l} \psi_{j_4}(X[t])$$

Following equation (18), in the expanded form, at every level, the filter coefficients $\widetilde{hr}_j$ is modified following the representation in equation (8), $$\widetilde{hr}_{j,l} = \frac{hr_l}{\sqrt{2^j}} \quad (19)$$

Leading from the expanded form in equation (18), the MODWT calculation leads to obtaining the pulse pressure, $\Delta P = X(t)$.

Figure 7:
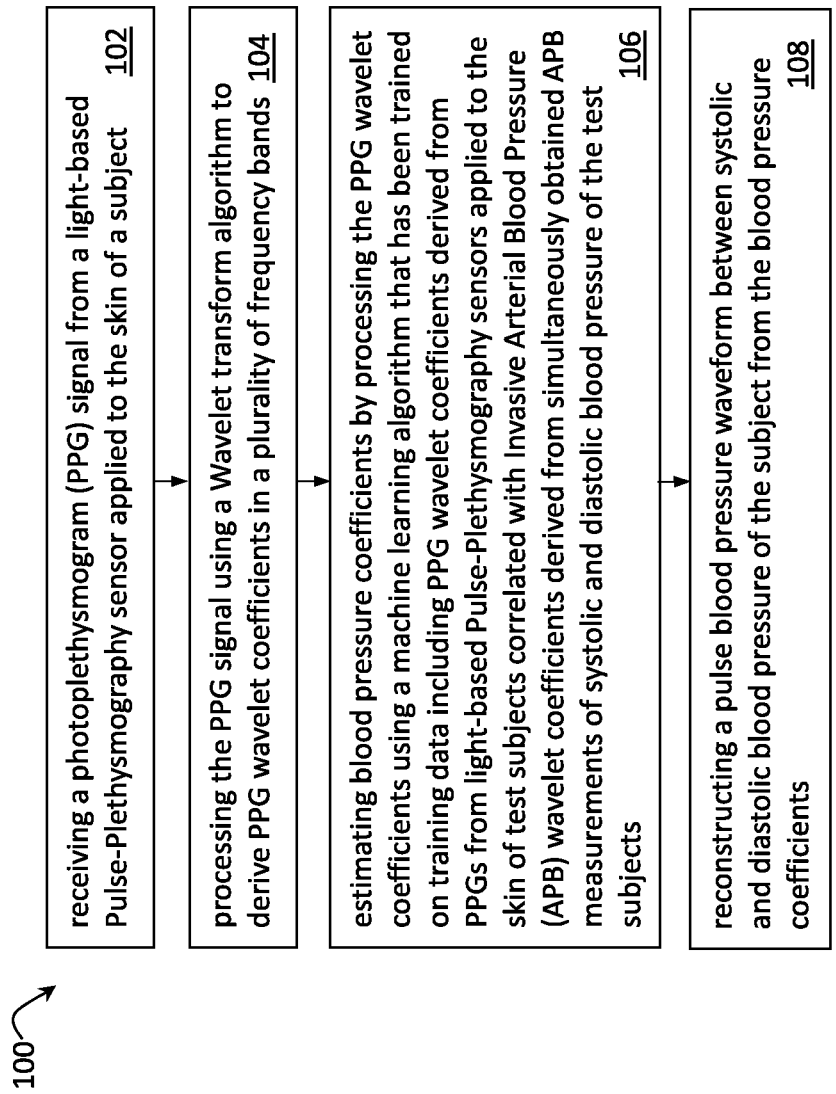
FIG. 7 is a flow chart showing a method of estimating blood pressure of a subject in operation in accordance with an embodiment of the present invention.

One embodiment of a method 100 of estimating blood pressure of a subject is summarised in FIG. 7. The method 100 shown in FIG. 7 includes the steps of: receiving 102 a photoplethysmogram (PPG) signal from a light-based Pulse-Plethysmography sensor applied to the skin of the subject; processing 104 the PPG signal using a Wavelet transform algorithm to derive PPG wavelet coefficients in a plurality of frequency bands; estimating 106 blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects; and reconstructing 108 a pulse blood pressure waveform between systolic and diastolic blood pressure of the subject from the blood pressure coefficients.

Figure 8:
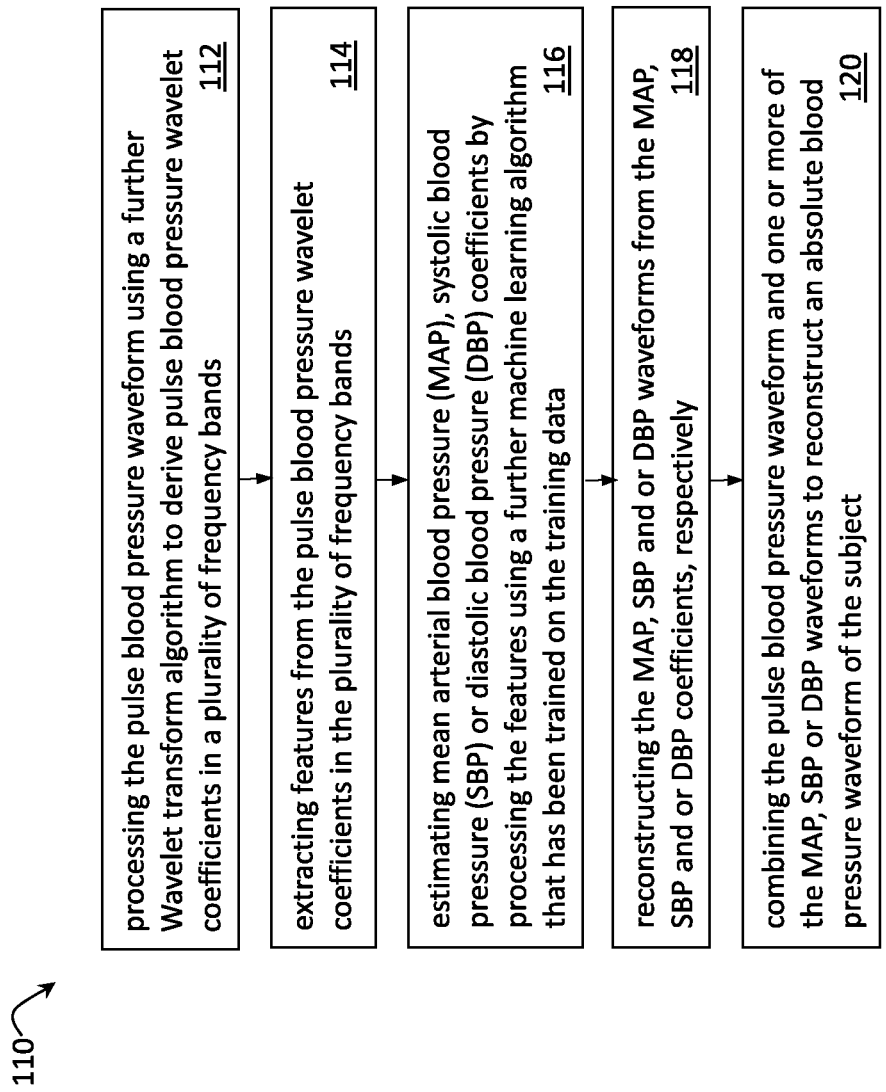
FIG. 8 is a flow chart showing a method of estimating blood pressure of a subject in operation in accordance with an embodiment of the present invention.

Another embodiment of the method 100 is shown in FIG. 8 in respect of the further method 110 of estimating blood pressure of a subject. The further method 110 includes the steps of: processing 112 the pulse blood pressure waveform using a further Wavelet transform algorithm to derive pulse blood pressure wavelet coefficients in a plurality of frequency bands; extracting 114 features from the pulse blood pressure wavelet coefficients in the plurality of frequency bands; estimating 116 mean arterial blood pressure (MAP), systolic blood pressure (SBP) or diastolic blood pressure (DBP) coefficients by processing the features using a further machine learning algorithm that has been trained on the training data; reconstructing 118 the MAP, SBP and or DBP waveforms from the MAP, SBP and or DBP coefficients, respectively; and combining 120 the pulse blood pressure waveform and one or more of the MAP, SBP or DBP waveforms to reconstruct an absolute blood pressure waveform of the subject.

Figure 9:
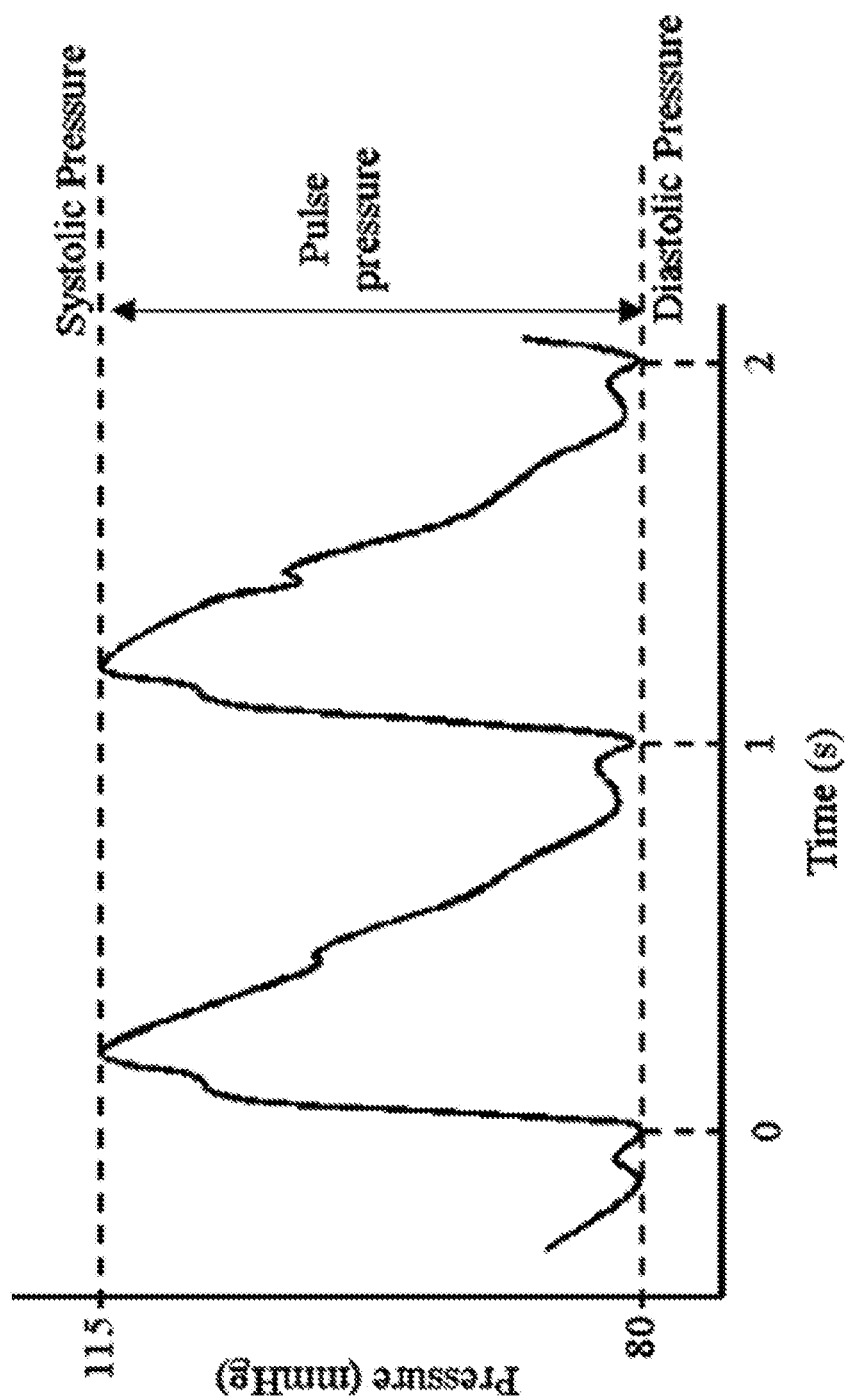
FIG. 9 is an example of a blood pressure waveform of a subject.

The absolute blood pressure waveform of a human subject is shown in FIG. 9. The maximum and minimum pressure are the Systolic (SBP) and Diastolic (DBP) blood pressures, respectively, which forms the Pulse Pressure Waveform. The mean of this waveform is the Mean Arterial Pressure (MAP). Embodiments of the present invention estimate the SBP, DBP and MAP waveforms over time using deep learning models. It can therefore be seen that, by combining the MAP, SBP or DBP waveforms, having pressure values, with the pulse pressure waveform, an absolute blood pressure waveform of the subject can be derived.

In respect of this method 110, the hardware used for the collection of bio-signals from a subject is a modified version of a Pulse-Plethysmography (PPG) sensor operating at a wavelength of 805 nm, also called the isosbestic wavelength, as above.

In an embodiment of this method 110 of estimating blood pressure, the acquired waveform from the PPG sensor is passed through a set of algorithms comprising: a Maximally Overlap Discrete Wavelet Transform algorithm; an LSTM Based Pulse Pressure Generation Algorithm; a Feature Matrix Generation algorithm; and a Conv-LSTM and Deep Neural Network Based Pressure Estimation algorithm.

FIG. 10 shows a summary of an embodiment of the method 110 of estimating blood pressure waveform from a combination of the abovementioned LSTM derived pulse pressure waveform algorithm and MAP waveform estimation algorithm.

In an embodiment, the method 100 and the further method 110 use hardware shown in FIG. 11. The hardware includes multiple LEDs and Photodiodes for acquisition of the PPG signal from any part of a subject's wrist. The hardware further includes a micro-controller to control the sensors with Bluetooth and WIFI capabilities for data transfer; a pulse-plethysmography PPG sensor chip. The multiple LEDs and Photo-diodes operate at wavelength range between 800-850 nm (isosbestic) and the hardware further includes multiplexers controlling the different pairs. In addition, the hardware includes an accelerometer to remove any motion artefacts, power supply units and a battery charging controller.

Figure 12:
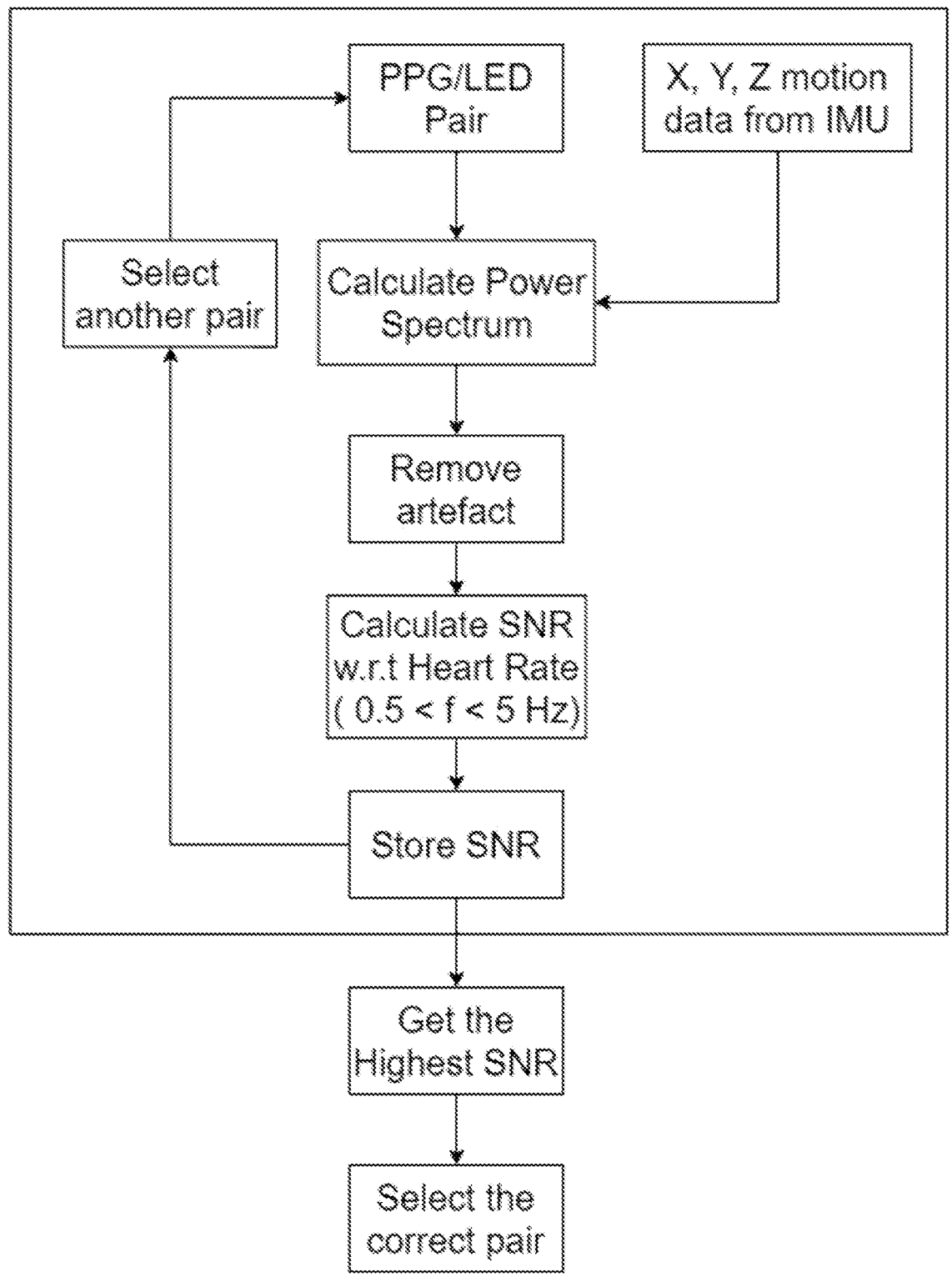
FIG. 12 is a block diagram showing a method of selecting a light source and a photodiode for estimating blood pressure of a subject in accordance with an embodiment of the present invention.

Multiple pairs or groups of LEDs and Photodiodes ensures that data collection is from any location of the wrist or limb of the subject where the device is placed. FIG. 12 shows a block diagram of the hardware in use.

A master micro-controller controls the pair of LED and photodiode to turn on and off based through an N-input multiplexer. The activated pair of the LED-photodiode is controlled by the PPG Sensor RX-TX control chip. This chip drives the LED at specific pulse-repetition frequency, drive voltage and current. It receives a signal from the selected photodiode. The signal is filtered and amplified. The processed signal is sent into the micro-controller which then decides the SNR of the signal.

The SNR of the signal will be affected by the motion artefact present or the location at which the pair of LED and photodiode is present. The motion artefact is calculated using the on-board 6 Axis IMU. The microcontroller runs the algorithm to select the most appropriate pair of the LED and photodiode, as embodied in the flow chart of FIG. 12. That is, the microcontroller calculates the SNR of each LED-photodiode pair along with a compensation value from the IMU sensor(s). The micro-controller than selects the pair of LED-photodiode with the best SNR.

An embodiment of the method of estimating blood pressure in use is described with reference to the flow chart of FIG. 13. As mentioned, the PPG sensors are formed of multiple pairs of LEDs and Photodiodes, which are operating at the isosbestic wavelength. The sensors are preferably disposed in a device that sits around the wrist and the sensors are equally spaced. This ensures that any motion of the device worn of the wrist does not hinder data collection. Further, it will ensure that the best Signal-To-Noise (SNR) PPG signal is collected and used, which will be highly dependent on the location of the radial or brachial artery on the subject and where the device is intended to be sitting on the subject.

In an initial cycle, all the pairs of LEDs and Photodiodes will be activated one after the other. A small batch of signals of a few seconds will be collected from each pair. The collected signal from each pair is processed to see the presence of:
  sinusoidal oscillations matching the centre frequency equivalent to heart rate;
  power spectrum analysis and comparison-higher powers around the desired frequency regions for better SNR; and
  lower power for harmonics, if the light waves are reflected from bones or tissues modifying or interfering with the centre frequency.

The pair of the LED and Photodiode adhering to the selection criteria will be considered to have the best SNR. The signal from this pair will be used subsequently for purpose of the estimation.

Figure 13:
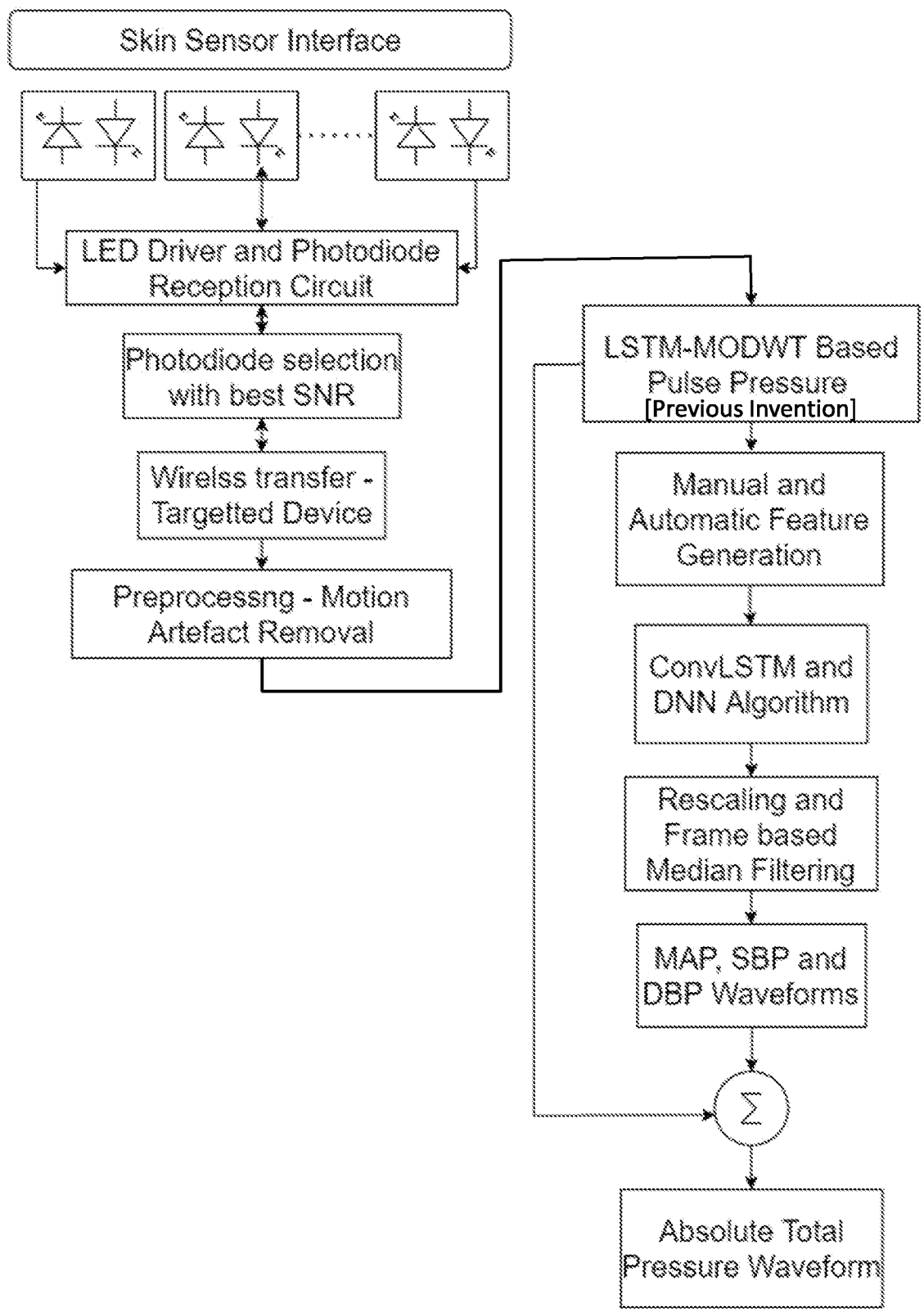
FIG. 13 is a flow chart showing a method of estimating blood pressure of a subject in operation in accordance with an embodiment of the present invention.

FIG. 13 further shows the signal from the PPG sensor being transmitted using a wireless method to a device which can undertake machine learning estimation, processing and reconstruction. The transfer can be through Bluetooth or WIFI. This is flexible and the mode of communication can be changed based on the target device, such as a mobile phone operating a dedicated application or a custom designed monitor.

FIG. 13 further includes the step of Pre-processing the signal from the PPG sensor. The initial pre-processing is followed from the reconstructing the pulse blood pressure waveform, which involves low pass filtering with a cut-off frequency at 20 Hz. In this frequency range, the expectation of higher physiological response is present.

In the LSTM-MODWT Based AP step, the pre-processed signal is passed through the LSTM based AP estimation algorithm which has been described above.

In the Feature Extraction step, the feature generation process involves automatic extraction of 2D features estimated from the LSTM algorithm, hand-designed specific features from PPG signal and hand-designed specific features from the estimated AP waveform. The three sets of features are processed, combined and concatenated to form the training and prediction algorithm for the method of estimating absolute blood pressure.

In the ConvLSTM and DNN algorithms step, the three sets of features from the feature extraction process are processed. The automatic 2D features are passed into the ConvLSTM algorithm while the hand-designed features are passed into multi-layer perceptrons (MLP). This results in forming three branches for the network getting three different sets of inputs. Subsequently, the algorithm ensures the concatenation of the three branches to form a convoluted semi-supervised structure.

The weights of the structure is learnt using the standard Back-Propagation algorithm. The final output of the structure has been designed to be either the SBP, DBP and MAP depending on what is being learnt. The optimisation of the structure with different hyper-parameters is based on the final output. The appropriate hyper-parameters are selected based on the performance for these three sets of the outputs.

In the Rescaling and Median Filtering step, following the estimation from the previous step, the output, be it SBP, DBP or MAP, is set to down-sampled vectors consisting N number of samples. In the step, N has been taken to be 1/10th the length of the actual input signal. A median filtering is carried out for every subsequent N length of the output SBP, DBP or MAP ensuring that any sudden changes in the estimated pressure output due to errors in the networks are minimised.

In the final Absolute Total Pressure Waveform step, the estimated waveforms of MAP, SBP and DBP are added to, or combined with, the AP waveform estimated and reconstructed according to the above described to generate the absolute (and continuous) blood pressure waveform of the subject.

The method 110 is described in more detail below. The method 110 commences with a training phase. As above, Invasive Arterial Blood Pressure (ABP) measurements and PPG signals are recorded from many patients simultaneously. As described with respect to FIG. 3, the PPG and ABP signals are passed through the Maximally Overlap Discrete Wavelet Transform (MODWT) algorithm and broken down into different bandwidths of frequencies between 0.5-8 Hz. The PPG MODWT waveform between specific frequency bandwidths is created into auto-regressive structures which are correlated to the ABP MODWT waveform between that specific bandwidth. The error is calculated after every iteration of training and the LSTM weights are updated.

Figure 19:
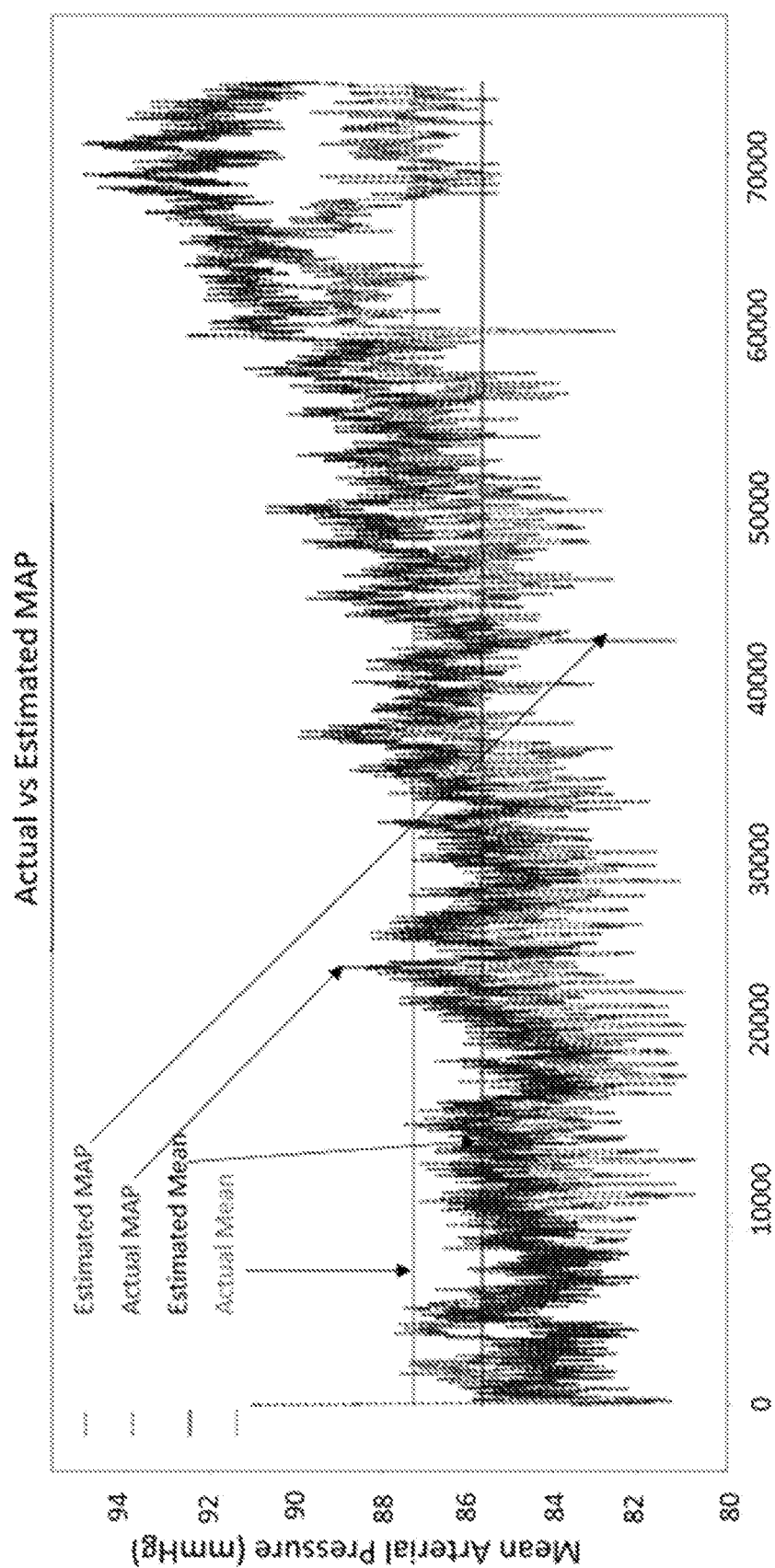
FIG. 19 is a diagram of a Mean Arterial Pressure estimation of a patient over 10 minutes.

The final result from this is the complex correlation time series networks relating the MODWT coefficients of PPG and ABP at different bandwidths as shown in the example FIGS. 19a-19c. The estimated waveforms shown in these FIGS. 19a-19c as subplot 2, 3, 4 and 5 represent the wavelet detailed coefficients which were estimated using the LSTM-MODWT at bandwidth 4-8 Hz ($\psi 4$), 2-4 Hz ($\psi 5$), 1-2 Hz ($\psi 6$) and 0.5-1 Hz ($\psi 7$). These outputs from the different bandwidths are combined using the inverse MODWT to reconstruct the pulse pressure waveform, AP.

Figure 14:
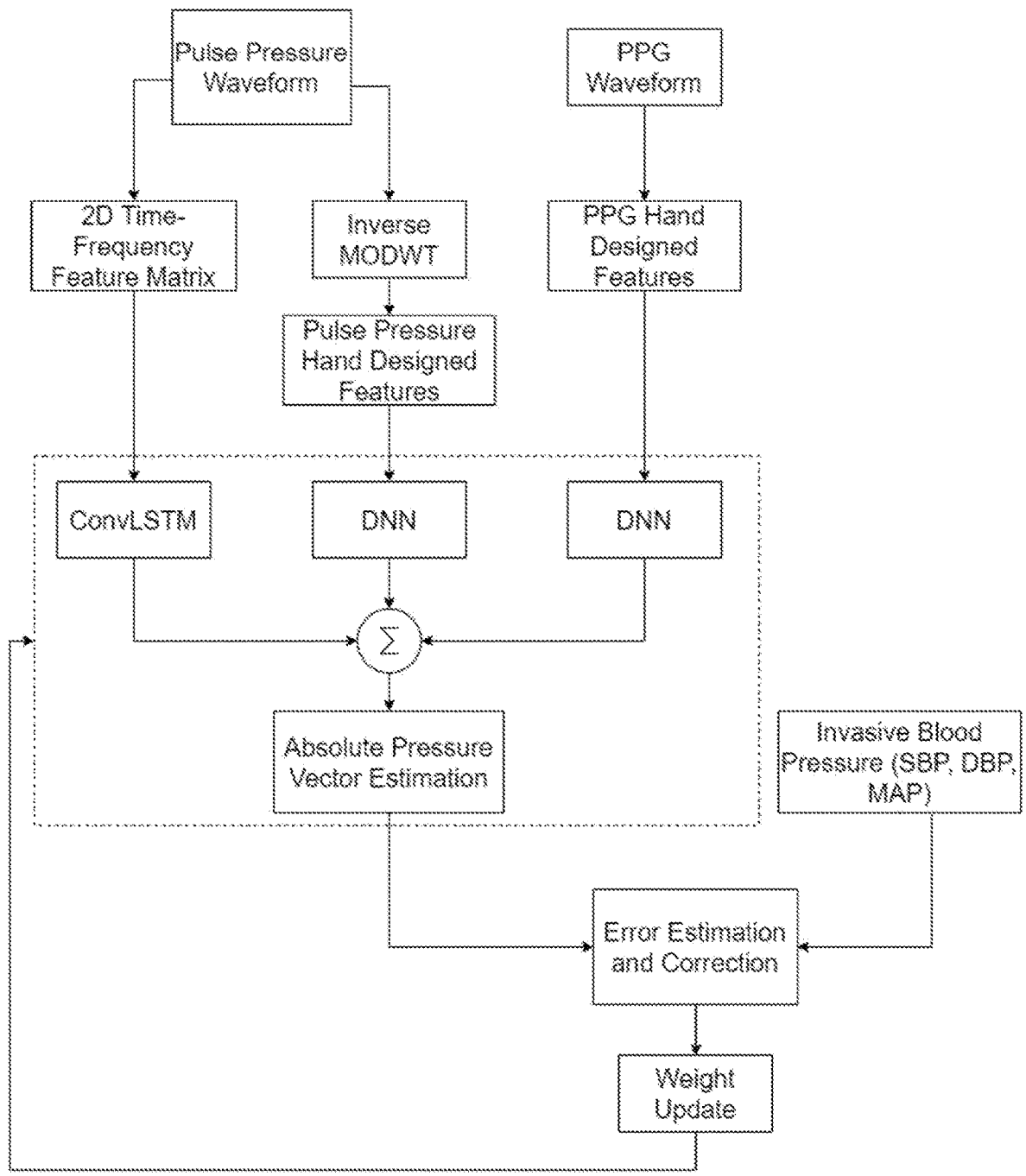
FIG. 14 is a flow chart showing a method of training a machine learning algorithm in accordance with an embodiment of the present invention.

The reconstructed pulse pressure waveform, AP, along with the PPG signal are used as input features for the method 110. The overall design of the training model of the method 110 is shown in FIG. 14. In particular, FIG. 14 shows the training phase of a Conv-LST-DNN based Absolute Pressure Estimation Model.

The estimated bands of the detailed coefficients are arranged into time-frequency 2D matrices which are used as features for the ConvLSTM network. The inverse MODWT reconstructed AP and PPG waveform are used to derive some of the hand designed features involving the time and amplitude values. These are passed into two separate branches of multi-layer perceptrons. All the branches are concatenated and the final output the expected estimate of the absolute pressure which may be either SBP, DBP or MAP. The error is calculated with the ground truth pressure values and the error is backpropagated to update the neural network weights.

Convolutional-LSTM Network

Convolutional-LSTM (ConvLSTM) is a hybrid of Convolutional Neural Networks (CNN) and Long Short Term Memory (LSTM) Recurrent Neural Networks. LSTMs have the capability of temporal forecasting. They are designed to remember the long and short state of the system, making them beneficial for time-series forecasting.

Figure 15:
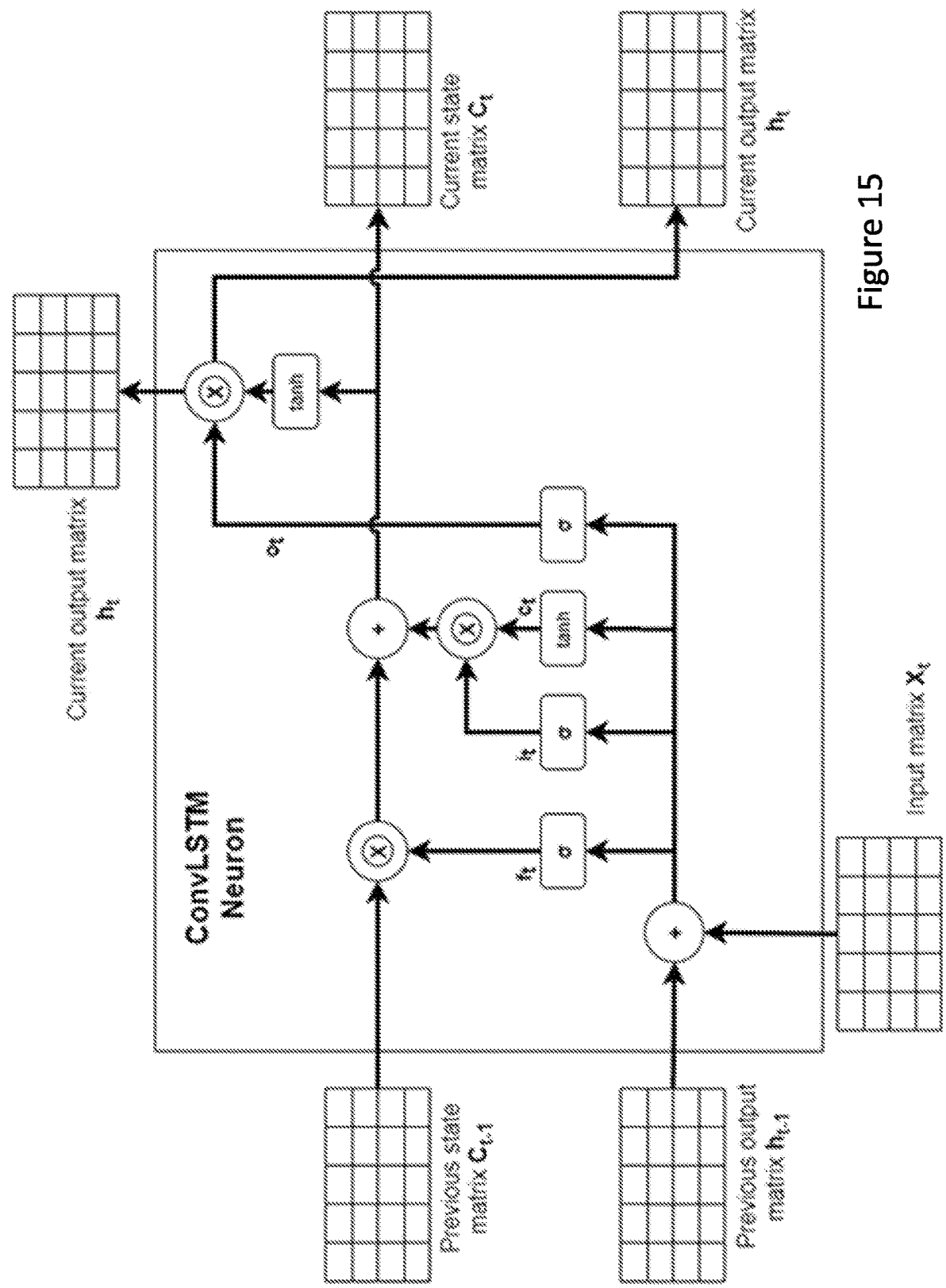
FIG. 15 is an example of a ConvLSTM neuron.

ConvLSTM consists of cells as shown in FIG. 15. The structure of a neuron of a ConvLSTM consists of forgetting, read, write and state gates but, instead of these being 1D vectors, they are 2D matrices. These gates have associated parameters—weights and biases—but a depth parameter is added as well with the number of filters similar to a CNN which are learnt through the process of feed-forward and back-propagation. The size of the weights and biases are dependent on the designer of the neural networks and the purpose for which it is designed. Preferably, the single ConvLSTM neuron has been assumed to have a units which are kept variable based on the depth and performance. These units are the matrix sizes of the parameters inside each cell which have to be learnt in the training process.

In the 2D form, the equations for the gates and the output is shown in equations (20)-(25), and the neuron shown in FIG. 15. All the multiplications have been replaced with the convolution between the inputs and the multiple number of filters.

$$f_t = \sigma(W_f \otimes h_{t-1} + U_f \otimes X_t + b_f) \tag{20}$$

$$i_t = \sigma(W_i \otimes h_{t-1} + U_i \otimes X_t + b_i) \tag{21}$$

$$\tilde{C}_t = \tanh(W \otimes h_{t-1} + U_o \otimes X_t + b) \tag{22}$$

$$o_t = \sigma(W_o \otimes h_{t-1} + Up \otimes X_t + b_o) \tag{23}$$

$$C_t = C_{t-1} \otimes f_t + i_t \otimes \tilde{c}_t \tag{24}$$

$$h_t = o_t \otimes \tanh C_t \tag{25}$$

where,
all the variables are 2D,
$f_t$=forget gate
$i_t$=selective read gate
$\sigma_t$=state gate
$o_t$=selective write gate
W=corresponding recurrent weights of the gates
b=corresponding biases of the gates
U=corresponding input weights of the gates
$X_t$=2D input matrix
$C_{t-1}$=previous cell state
$h_{t-1}$=previous cell
$h_t$=current cell output The ConvLSTM neuron as shown in FIG. 15 takes a 2D matrix of input at specific time index and passes it through four gates. But unlike LSTM which consists of four 1D weight vectors each of length n, the ConvLSTM consists of n 2D filters, which makes it 4×n 2D filters to be learnt for each neuron during the training process.

Passing of 1 feature matrix, $(X_t)$ of dimension $D_1 \times H_1$ through a n number of 2D filters in a gate of shape Kx K∈{K=N} results in 3D tensors of shape of $n \times D_2 \times H_2$. These are the number of features extracted for each gate after convolution, at a timeframe of t=tn. This has a capacity to derive extremely deep and abstract features which would have been missed in a simple neural network. The shape of $D_2$ and $H_2$ highly depends on the hyperparameters selected for the ConvLSTM, especially the dimension of filter K, stride of the filter, zero padding and number of filters h. Usually, keeping the filter dimension K=3, stride as 1, zero padding as 1 (which refers to padding the boundaries in order to preserve the same shape of the output as that of the input) and number of filters as 64, the output dimension from each gate would calculate to be:

$$D_2 = \frac{D_1 - K + 2 \times \text{Padding}}{\text{Stride}} + 1 = 4 \quad (26)$$

$$H_2 = \frac{H_1 - K + 2 \times \text{Padding}}{\text{Stride}} + 1 = (H_1 - 3 + 2) + 1 = H_1 \quad (27)$$

Hence, with this example one gate would result in 64×4× $H_1$ number of features. Here, $H_1$ depends on the length of the feature vector in time domain. Undertaking the operations from each gates having the dimension of 64×4×$H_1$ shown in equations (20)-(25) would result in $h_t$ and $C_t$ as the output from the neuron of dimensions 64×4×$H_1$.

Figure 16:
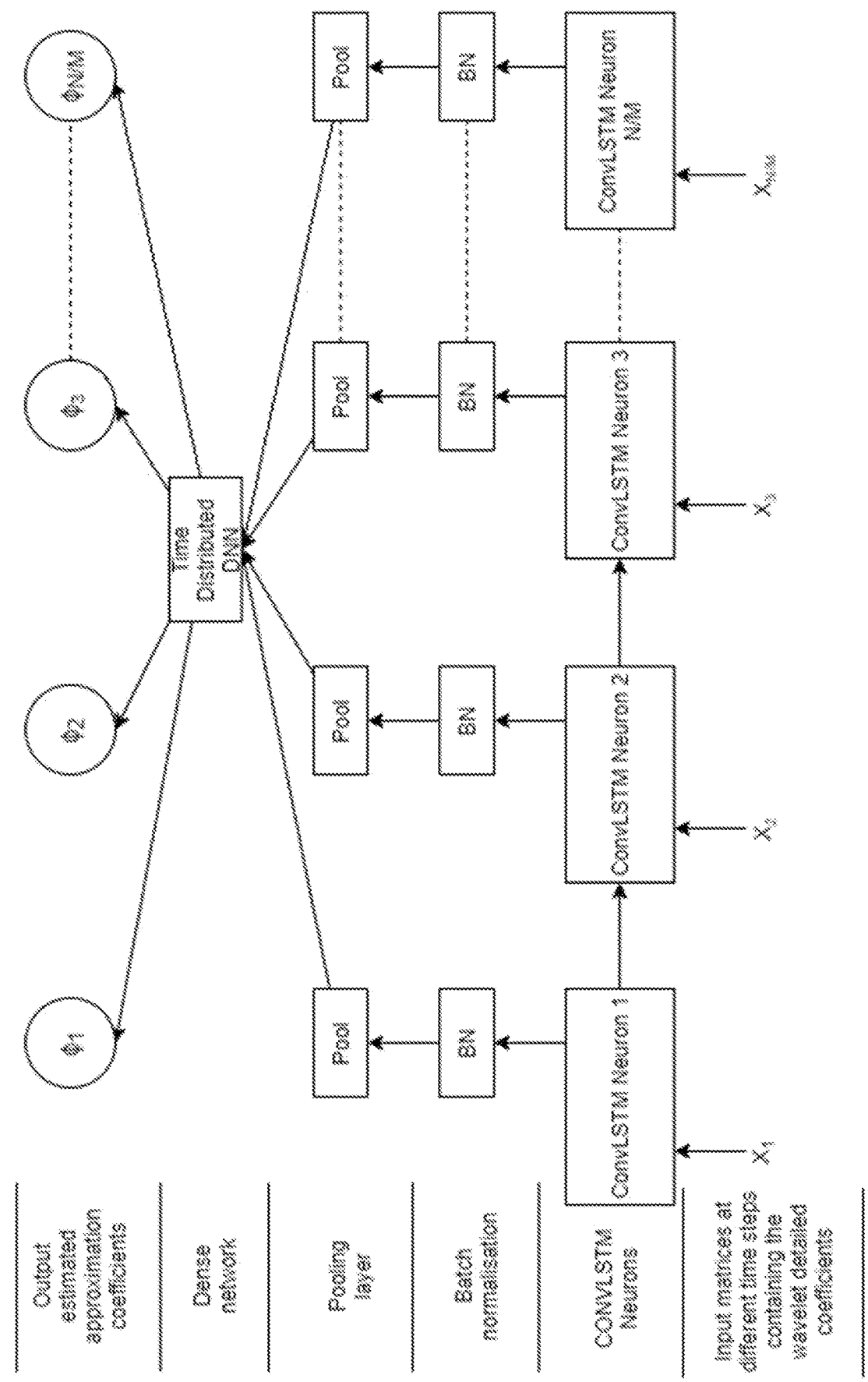
FIG. 16 is an example of a multi-layered ConvLSTM structure.

In a multi-layer structure, the number of time inputs depends on the number of frames the inputs have been divided. Considering each frame of length x, then x number of ConvLSTM cells will be stacked sequentially, similar to the LSTM network as shown in FIG. 16. This further would lead to x number of output matrices for $h_t$.

Figure 17:
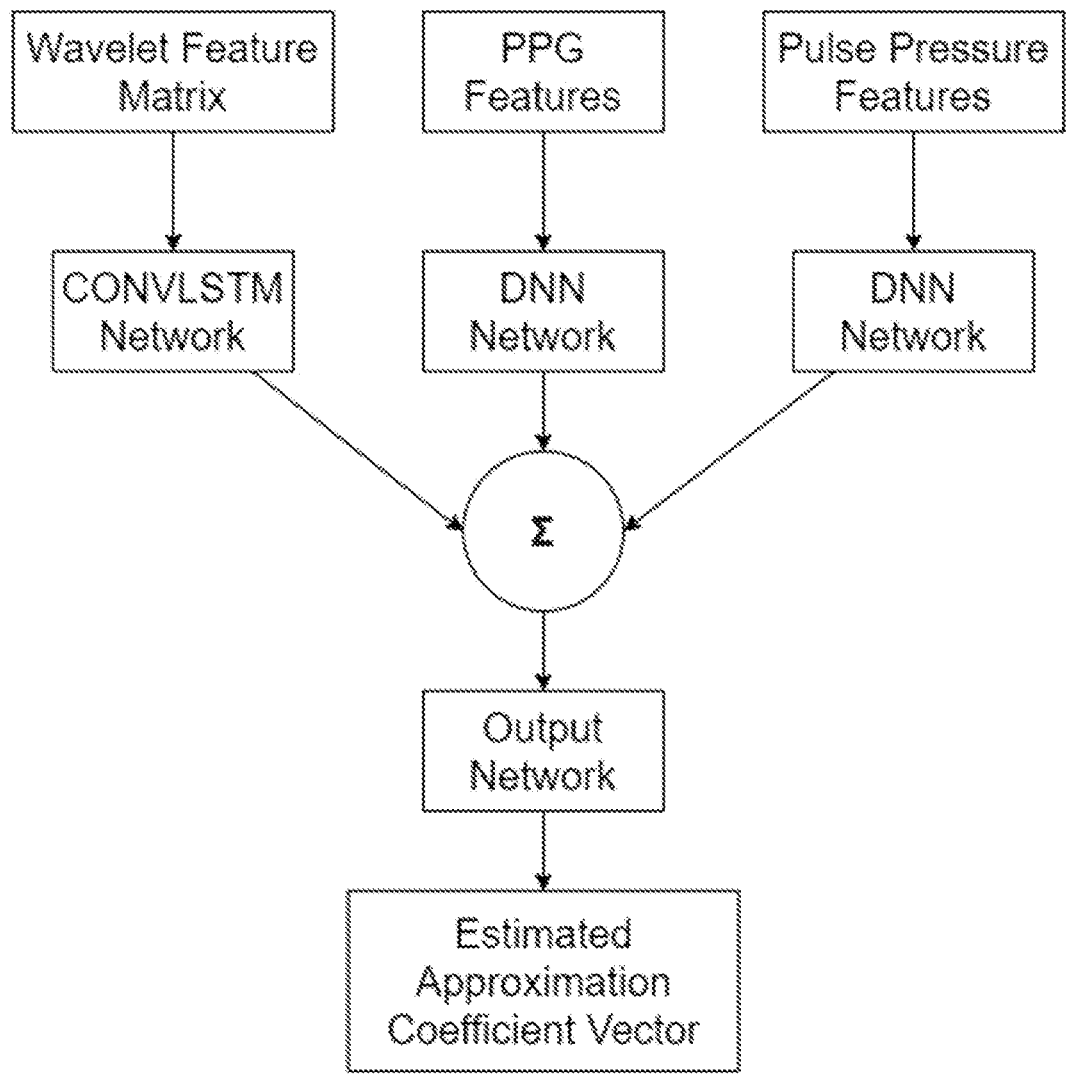
FIG. 17 is a flow chart showing a method of estimating blood pressure of a subject in operation in accordance with an embodiment of the present invention.
Figure 18A:
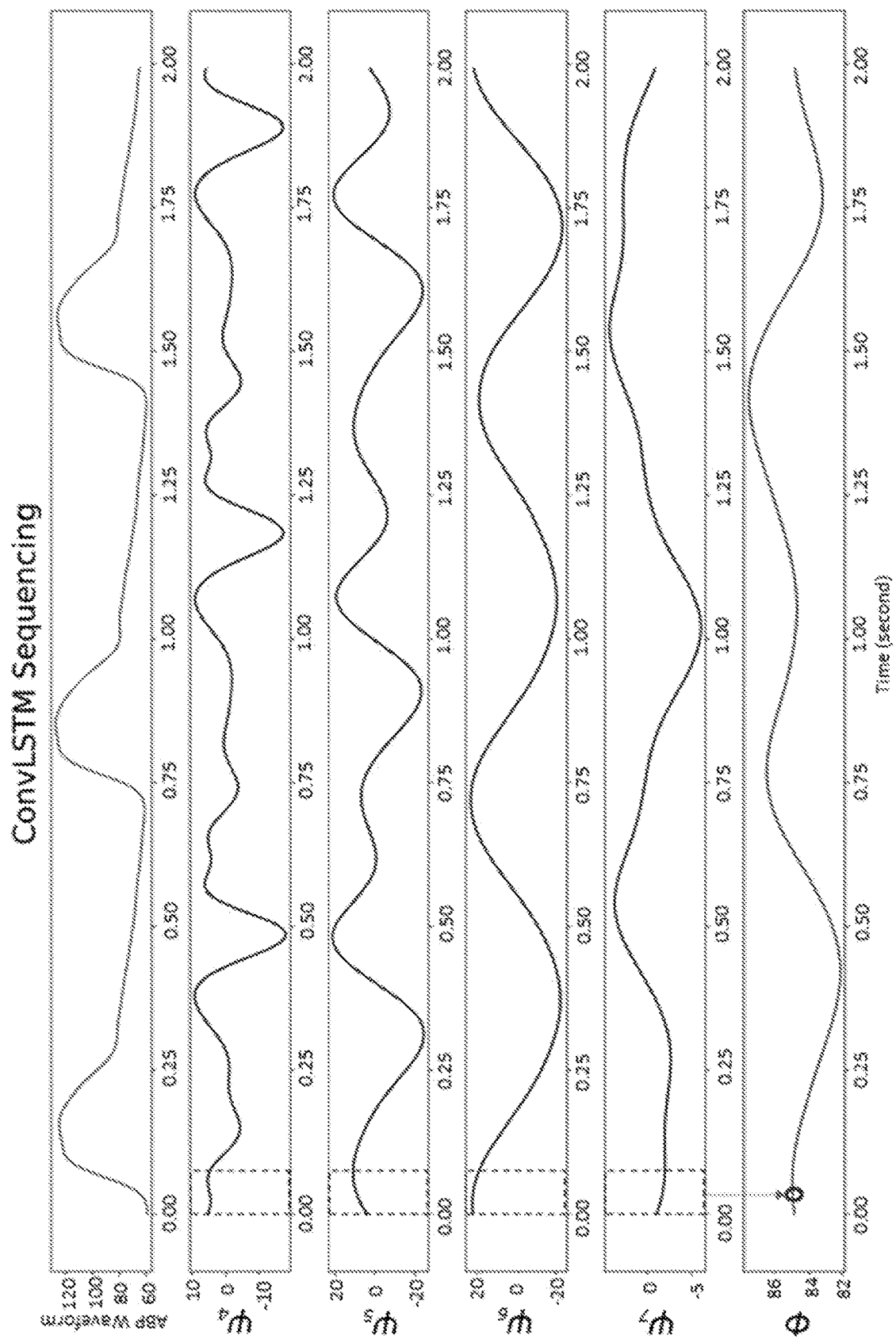
FIG. 18a is a diagram showing ConvLSTM sequencing for sequence 1.
Figure 18B:
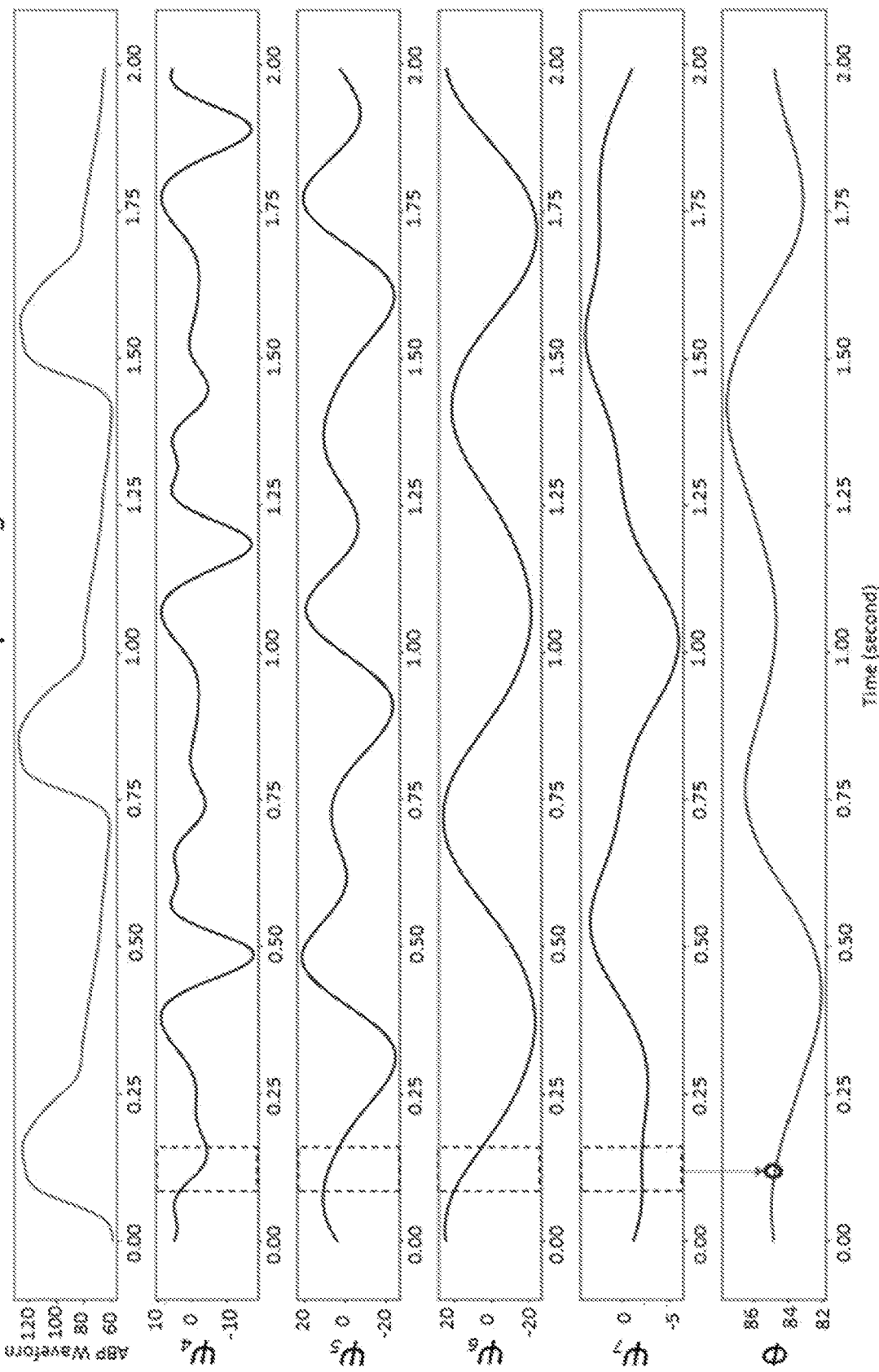
FIG. 18b is a diagram showing ConvLSTM sequencing for sequence 2.
Figure 18C:
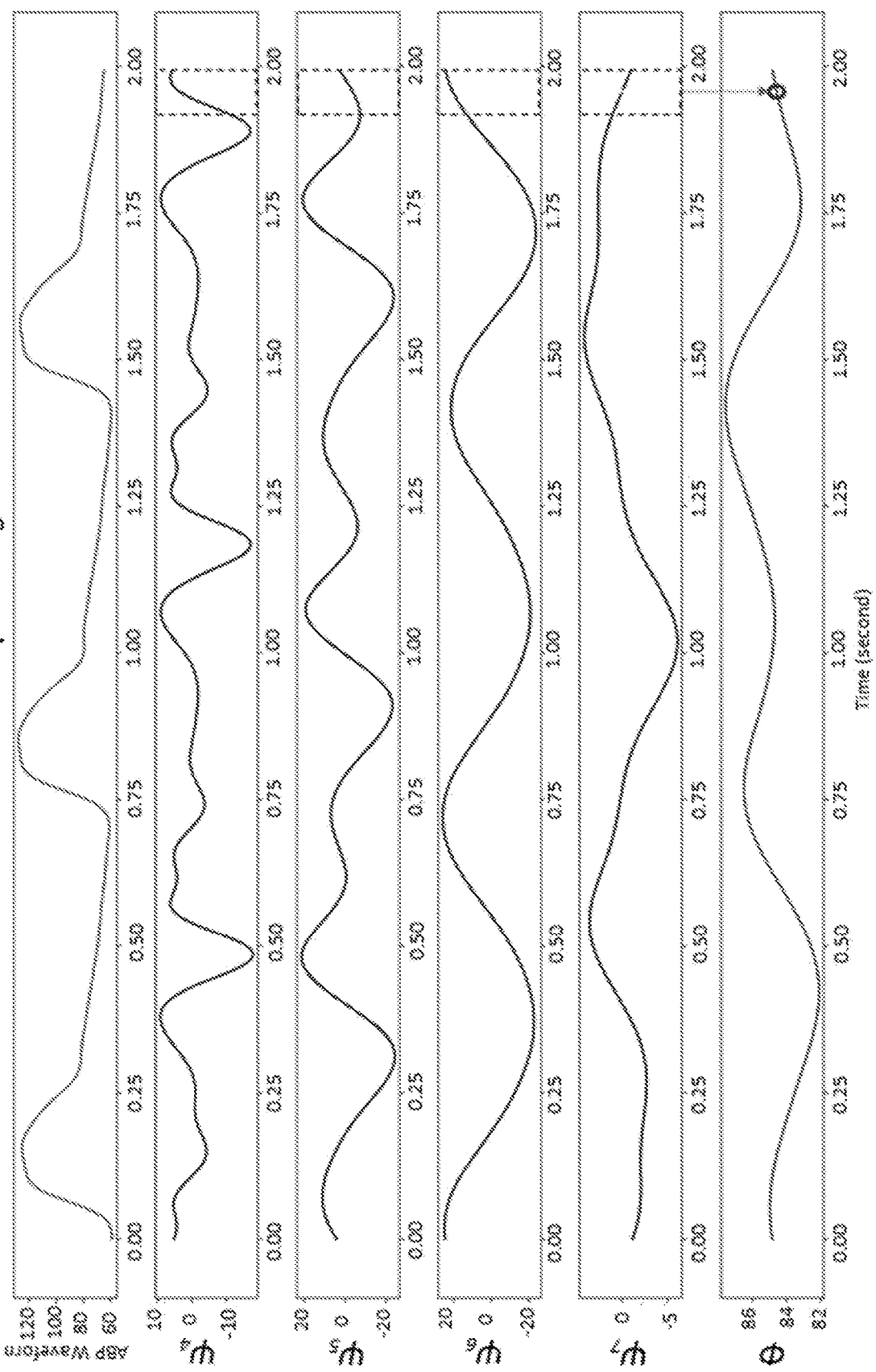
FIG. 18c is a diagram showing ConvLSTM sequencing for sequence N.

The output from each neuron has features estimated from the 2D matrix, which when passed through the batch normalisation and subsequently pooling layer are reduced in spatial shape. In the final step, the output from x frames are flattened and passed through a dense layer as a vector to run the regression analysis. The dense layer is called a Time Distributed layer. This takes the flattened inputs from each time step and generate a vector of time sequence output as shown in the FIG. 17.

Data Structuring and Features

The output from the n LSTM networks are n vectors of length L. In an embodiment, n=4 and L=250. n represents the number of bandwidths the LSTM outputs which are divided into 4 regions consisting of: 0.5-1 Hz, 1-2 Hz, 2-4 Hz and 4-8 Hz. The length of the signal chosen as this is based on the sampling frequency, which in this case is $F_s$=125 Hz. This captures 2 second of the PPG signal and the corresponding AP from the LSTM output. The n number of vectors are concatenated into n×L matrix, $$\psi^{ABP}[k] = \begin{bmatrix} 0 \\ 0 \\ 0 \\ \psi_1[X[t]] \\ \psi_2[X[t]] \\ \psi_3[X[t]] \\ \psi_4[X[t]] \end{bmatrix} \quad (28)$$

where:
$\psi(ABP[t])$=$\log_2 L \times L$ matrix of the decomposition wavelet coefficients
$\psi_n(.)$=vector output from the nth LSTM models
X(t)=feature matrix for LSTM at particular bandwidth of frequency The presence of the zero padding are due to the higher frequency domains, greater than 16 Hz, which have not been considered to be region of interest of the PPG-blood pressure correlation.

In order to reconstruct the signal, the inverse MODWT of the signal in equation (28) was taken. As discussed above, the output was passed through a Daubechies filter with 4 vanishing moments, db4. Each estimated vector is convolved with the filter and added in order to reconstruct the pulse pressure. A simplified version of the equation process is shown in the equation (29).

$$\Delta P(t) = \sum_{i=0}^{n} [\psi(ABP[t])_t \otimes \tilde{h}_r] \quad (29)$$

where:
$\Delta P(t)$=pulse pressure
$h_r$=Daubechies reconstruction filter coefficients In the method 110, the $\psi(ABP[f])$ equation (28) as well as the $\Delta P(t)$ equation (29) were used in the generation of the feature matrix.

ConvLSTM cells accept 2D matrices as inputs. In this case, the estimated non-zero MODWT coefficients of ABP as shown in equation (28) were structured into inputs. The outputs on the other hand were the approximation coefficients of the ABP expected to be estimated from the machine learning algorithm.

The estimated detailed wavelet coefficients following equation (28) of signal of length L comes out to be of shape 4×N shown in equation (30). Where, as discussed, the estimated sequence-to-sequence relationship was developed for four levels consisting of highest energy from above.

$$\begin{bmatrix} \psi_1(\overline{ABP[t]}) \\ \psi_2(\overline{ABP[t]}) \\ \psi_3(\overline{ABP[t]}) \\ \psi_4(\overline{ABP[t]}) \end{bmatrix} = \begin{bmatrix} \psi_1(ABP[0]) & \psi_1(ABP[1]) & \dots & \psi_1(ABP[L]) \\ \psi_2(ABP[0]) & \psi_2(ABP[1]) & \dots & \psi_2(ABP[L]) \\ \psi_3(ABP[0]) & \psi_3(ABP[1]) & \dots & \psi_3(ABP[L]) \\ \psi_4(ABP[0]) & \psi_4(ABP[1]) & \dots & \psi_4(ABP[L]) \end{bmatrix} \quad (30)$$

The 2D matrix in equation (30) was structured into 4×M dimensional smaller 2D feature matrices with non-overlapping parts. Here M is the fraction of signal length L. This further resulted in L/M number of total feature matrices for a signal. Mathematically one feature matrix is shown in equation (31).

$$\begin{bmatrix} \psi_1(\overline{ABP[t]}) \\ \psi_2(\overline{ABP[t]}) \\ \psi_3(\overline{ABP[t]}) \\ \psi_4(\overline{ABP[t]}) \end{bmatrix} = \begin{bmatrix} \psi_1(ABP[t]) & \psi_1(ABP[t+1]) & \dots & \psi_1(ABP[t+M]) \\ \psi_2(ABP[t]) & \psi_2(ABP[t+1]) & \dots & \psi_2(ABP[t+M]) \\ \psi_3(ABP[t]) & \psi_3(ABP[t+1]) & \dots & \psi_3(ABP[t+M]) \\ \psi_4(ABP[t]) & \psi_4(ABP[t+1]) & \dots & \psi_4(ABP[t+M]) \end{bmatrix} \quad (31)$$

Here, n E 1, 2, . . . , L/M. In the embodiment, M is taken to be 10. This results in providing 10 samples of the wavelets approximation coefficient matrix.

The output vector is the approximation coefficients of the signal of length L or the bandwidth of the signal between 0-0.5 Hz represented by ¢. This ¢ can also be either the upper or the lower envelope representing the SBP or DBP waveform of the blood pressure. This vector is of length L. The approximation coefficients vector was sub-divided into L/M output vectors. With the input feature being of dimension 4×M, the output was selected to be the median location of 1×M approximation coefficients. This was done in order to incorporate a non-causal model with the output depending on a few past samples and a few future samples shown in equation (32).

$$y = \phi\left(ABP_{\frac{t_n+M}{2}}\right) \quad (32)$$

where $t_n$ is the starting location of each of the feature matrices

Hence, the output vector from the ConvLSTM is expected to be an N/M length of approximation coefficients shown in equation (33).

$$y = \left[\phi\left(ABP_{\frac{t_1+M}{2}}\right)\phi\left(ABP_{\frac{t_2+M}{2}}\right) \cdots \phi\left(ABP_{\frac{t_{\frac{N}{M}}+M}{2}}\right)\right] \quad (33)$$

A diagrammatic representation is shown in FIGS. 19a-19c. The estimates ψ4-ψ7 are the estimated wavelet bands as described above. These are concatenated in a 2D form. A window moves over creating a correlation with the φ approximation coefficients vector at the median point as shown in FIGS. 19a-19c. This entire process occurs within the ConvLSTM network.

Deep Neural Network (DNN) Features

In an embodiment, hand-designed features are selected for further blood pressure estimation. These selected features selected were heuristic with the number of features ranging from 5 to 50, all extracted manually. The features include both common features based on time and amplitude, such as rise time, fall time, rising inflection time, falling inflection time, area under the rising curve, area under the falling curve and heart rate (centre frequency of the signal), and features from the current approximation coefficient estimation algorithm. By using these features, the accuracy of the estimation of blood pressure is improved.

But the addition of these features pose a problem to the ConvLSTM Network as they take time-series 2D matrices of the detailed coefficients. One possibility was training of different networks, one based on the ConvLSTM architecture and one based on the deep networks with hand-designed features. This is the method of Ensemble Learning. The estimated accuracy will be the weighted average of the two different models. The problem with this technique is the learned weights of each model will be independent from each other. As the algorithm has to share the output error from the back propagation, a different architecture was selected to be used.

In this embodiment, multiple models were used which are concatenated at the end of the process to estimate a single output. This is based on the theory of developing a functional architecture rather than a sequential architecture. In a Sequential Architecture, the data flows from the input to output without branching, while in a Functional Architecture, branches are present making it possible to further add different inputs which have a possibility of improving the network accuracy. In this embodiment, functional architecture is used.

A deep neural network was used in this case which has been designed to incorporate selected (hand-designed) features from:
PPG waveform; and
Pulse pressure waveform.

Other important point to consider is the absolute values of time and amplitudes will vary significantly among the signals. Instead of taking these absolute values, ratios were obtained with respect to a total length of the window of the signal in cases of time related features and range of the signal in case of amplitude related the features.

A total of 13 features from PPG were obtained which are listed below. These features were averaged for a signal with N heart cycles of PPG:

1. Total Window Time (WT)—time duration of one entire cycle of the PPG signal.
2. Rise Time Ratio (RTR)—the ratio of the time taken for the PPG to rise to the maximum value to that of the WT.
3. Fall Time Ratio (FTR)—the ratio of the time taken for the PPG to fall from the maximum to minimum value to that of the WT.
4. Rise Inflection Time Ratio (RITR)—the ratio of the time taken to reach the first rising inflection point to that of the WT.
5. Fall Inflection Time Ratio (FITR)—the ratio of the time taken to fall from the maximum value to the falling inflection point to that of the WT.
6. Heart Rate Frequency (HRF)—the instantaneous heart rate calculated from the N heart cycles.
7. Pulse Plethysmogram Intensity Ratio (PIR)—the ratio of the maximum to the minimum value of the PPG signal.

$$PIR = \frac{V_{PPG_{MAX}}}{V_{PPG_{MIN}}} \quad (34)$$

8. Rising Inflection Point Relative Height (RIPRH)—the ratio of the PPG amplitude at the rising inflection point to the maximum height.
9. Falling Inflection Point Relative Height (FIPRH)—the ratio of the PPG amplitude at the falling inflection point to the maximum height.
10. Systolic Area Ratio (SAR)—the area under the rising part of the PPG signal to the total area under the curve.
11. Diastolic Area Ratio (DAR)—the area under the falling part of the PPG signal to the total area under the curve.
12. Systolic to Diastolic Area Ratio (SDAR)—the ratio of the SAR to DAR.
13. AC to DC Ratio (ADR)—the ratio of the PPG amplitude to the RMS of the signal:

$$ADR = \frac{PPG_{max} - PPG_{min}}{rms(PPG)} \quad (35)$$

From the Pulse Pressure, a total of 7 features related to the amplitude were selected listed below:
1. Maximum of the pulse pressure
2. Minimum of the pulse pressure
3. Amplitude of the pulse pressure
4. Systolic area ratio 5. Diastolic area ratio
6. Rising inflection height
7. Falling inflection height.

Integration—ConvLSTM and DNN Networks

The ConvLSTM and the DNN networks have been designed in a functional structure with three branches. One branch taking the input as the time series wavelet matrices shown in equation (31). The second branch takes the PPG features as the input while the third branch takes the pulse pressure features as input.

The output is the estimation of the approximation coefficient vector shown in equation (33). The overall network structure with the branched inputs are further shown in FIG. 17.

The output from the time distributed dense of the ConvLSTM is concatenated with the outputs of the two DNN in the functional network structure.

The concatenated output is passed through multiple layers of hidden neurons in Output Network. Finally, the loss is calculated between the ground truth approximation coefficients and the predicted approximation coefficients of the batch during training and backpropagated with the error.

The final trained model is expected to estimate a vector sequence of length L/M number of approximation coefficients. Flexibility of the design also allows to train the model to estimate the vector output for SBP or DBP instead of the ¢ which represents the MAP.

Post Processing and Median Filtering

The final output ϕ is a vector L/M, which in the current case has been taken to be $$\left\lfloor \frac{250}{10} \right\rfloor - 1 = 24.$$

The negative 1 is added in the current case to have an even sample length which can be used in creating a moving median filter. Instead of giving a capture of MAP, SBP or DBP—based on what the ϕ is learnt to be, a median filtering is carried out by estimating on the subsequent signal of length L.

In an embodiment, L is taken to be of length of 2 seconds (sampling frequency=125 Hz). If a signal of length 10 seconds is collected from the PPG, the signal is broken down into 40 overlapping frames 2 seconds worth of signal, with 75% overlap. This overlap can be more or less. Each sequence is used for the estimation of ϕ vector, resulting in 40 vectors in the current instance.

A moving median filter is applied across the overlapped signal. The median filter has the advantage of being less prone to outliers as compared to the moving average filter. However, the flexibility of the design allows to use moving average filter. The median filter:

pads the current signal with i x B zeros;
pads the previous signal with B zeros (this ensures equal length of the signal whose median is calculated);
takes the median of the resulting two signals; and
stores the median filter as the previous signal to be used for subsequent frame median calculation.

A resulting Median Filtered MAP estimation for a subject is shown in FIG. 20 for a length of 10 minutes. The estimated waveform has been obtained by ConvLSTM algorithm combined with the LSTM-MODWT algorithm.

Reconstruction

The final reconstruction of the signal, as depicted in the overall design FIG. 13, is the output from the LSTM-MODWT algorithm from above—the pulse pressure waveform, combined with (added to) the output of the MAP, SBP or DBP waveforms. This generates the absolute blood pressure output:

$$P(t) = \Delta P(t) + \phi \qquad (36)$$

It will be appreciated by those persons skilled in the art that further aspects of the methods 100 110 will be apparent from the above description of the system 10. Further, those persons skilled in the art will also appreciate that the methods 100 110 is embodied in software, or program code, that can be supplied to the computer 14 in a number of ways, such as on a memory.

Finally, it is to be understood that various alterations, modifications and/or additions may be introduced into the constructions and arrangements of parts previously described without departing from the spirit or ambit of the invention.

The invention claimed is:

1. A method of estimating blood pressure of a subject, the method including:
   receiving a photoplethysmogram (PPG) signal from a light-based Pulse-Plethysmography sensor applied to the skin of the subject;
   processing the PPG signal using a Wavelet transform algorithm to derive PPG wavelet coefficients in a plurality of frequency bands;
   estimating blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects; and
   reconstructing a pulse blood pressure waveform between systolic and diastolic blood pressure of the subject from the blood pressure coefficients.

2. A method according to claim 1, further including processing selected ones of the PPG wavelet coefficients for processing using the machine learning algorithm based on an energy level present at each of the frequency bands exceeding a threshold level.

3. A method according to claim 2, further including providing the selected ones of the PPG wavelet coefficients in a 2-Dimensional matrix of features to the machine learning algorithm.

4. A method according to claim 3, wherein each column of the 2-Dimensional matrix is autoregressive incorporating near past and near future samples of the selected ones of the PPG wavelet coefficients.

5. A method according to claim 1, wherein the machine learning algorithm is a Recurrent Neural Network (RNN) algorithm.

6. A method according to claim 5, wherein the RNN algorithm is a Long short-term memory (LSTM) model.

7. A method according to claim 6, further including processing the PPG wavelet coefficients using multiple LSTM models.

8. A method according to claim 7, further including reconstructing output of the multiple LSTM models to form the pulse blood pressure waveform using an inverse Wavelet transform algorithm.

9. A method according to claim 8, wherein the Wavelet transform algorithm is a Maximally Overlapped Discrete Wavelet Transform (MODWT) algorithm, and the method further includes reconstructing the pulse blood pressure waveform using an inverse MODWT algorithm.

10. A method according to claim 1, further including pre-processing the PPG signal before processing using the machine learning algorithm by low-pass filtering the PPG signal with a cut-off frequency for the frequency bands.

11. A method according to claim 1, further including:
processing the pulse blood pressure waveform using a further Wavelet transform algorithm to derive pulse blood pressure wavelet coefficients in a plurality of frequency bands;
extracting features from the pulse blood pressure wavelet coefficients in the plurality of frequency bands;
estimating mean arterial blood pressure (MAP), systolic blood pressure (SBP) or diastolic blood pressure (DBP) coefficients by processing the features using a further machine learning algorithm that has been trained on the training data; and
reconstructing the MAP, SBP and or DBP waveforms from the MAP, SBP and or and/or DBP coefficients, respectively.

12. A method according to claim 11, further including combining the pulse blood pressure waveform and one or more of the MAP, SBP or DBP waveforms to reconstruct an absolute blood pressure waveform of the subject.

13. A method according to claim 11, wherein the further machine learning algorithm is a Convolutional Long short-term memory (ConvLSTM) network and the features are a 2-Dimensional feature matrix including temporal and spatial features of the pulse blood pressure wavelet coefficients.

14. A method according to claim 13, further including estimating intermediate MAP, SBP or DBP coefficients using the ConvLSTM network.

15. A method according to claim 14, further including:
selecting features of the PPG signal and the pulse blood pressure waveform; and
estimating further intermediate MAP, SBP or DBP coefficients by processing the features of the PPG signal and the pulse blood pressure waveform using deep neural networks, respectively, that have been trained on the training data.

16. A method according to claim 15, further including: concatenating the intermediate and further intermediate MAP, SBP or DBP coefficients to form a concatenated output vector; and passing the output vector through multiple layers of hidden neurons in an output network to generate the estimated MAP, SBP or DBP coefficients.

17. A method according to claim 1, wherein the light-based Pulse-Plethysmography sensor includes a light source having an emission wavelength and a photodiode having a detection wavelength, wherein the emission wavelength and the detection wavelength are around an isosbestic wavelength where oxygenated and deoxygenated blood absorbs the same amount of light.

18. A method according to claim 17, wherein the light source is an Infrared (IR) light source.

19. A method of monitoring blood pressure of a subject, the method including: applying a light-based Plethysmography sensor to the skin of the subject for a period of time; and estimating the blood pressure of the subject according to the method of claim 1 at designated intervals over the period time.

20. A system for estimating blood pressure of a subject, the system including:
a light-based Pulse-Plethysmography sensor configured to be applied to the skin of the subject to generate a photoplethysmogram (PPG) signal;
a processor in data communication with the sensor;
a memory; and
software resident in the memory and accessible to the processor, the software including a series of instructions executable by the processor to configure the processor to:
process the PPG signal using a Wavelet transform algorithm to derive PPG wavelet coefficients in a plurality of frequency bands;
estimate blood pressure coefficients by processing the PPG wavelet coefficients using a machine learning algorithm that has been trained on training data including PPG wavelet coefficients derived from PPGs from light-based Pulse-Plethysmography sensors applied to the skin of test subjects correlated with Invasive Arterial Blood Pressure (ABP) wavelet coefficients derived from simultaneously obtained ABP measurements of systolic and diastolic blood pressure of the test subjects;
reconstruct a pulse blood pressure waveform between systolic and diastolic blood pressure of the subject from the blood pressure coefficients; and
output the pulse blood pressure waveform to a display.

* * * * *